(12) United States Patent
Imanaka

(10) Patent No.: US 7,537,678 B2
(45) Date of Patent: May 26, 2009

(54) DETECTING ELECTRODE AND NITROGEN OXIDE SENSOR USING THE SAME

(75) Inventor: Nobuhito Imanaka, Kawanishi (JP)

(73) Assignee: Japan Science and Technology Agency, Saitama (JP)

( * ) Notice: Subject to any disclaimer, the term of this patent is extended or adjusted under 35 U.S.C. 154(b) by 685 days.

(21) Appl. No.: 10/512,307

(22) PCT Filed: Apr. 18, 2003

(86) PCT No.: PCT/JP03/05021

§ 371 (c)(1),
(2), (4) Date: Oct. 25, 2004

(87) PCT Pub. No.: WO03/091719

PCT Pub. Date: Nov. 6, 2003

(65) Prior Publication Data

US 2005/0205423 A1 Sep. 22, 2005

(30) Foreign Application Priority Data

Apr. 25, 2002 (JP) ............................. 2002-124946

(51) Int. Cl.
*G01N 27/26* (2006.01)
(52) U.S. Cl. ...................... 204/431; 204/421; 204/424; 204/426; 204/280; 204/290.01; 204/290.1; 205/775; 205/780.5; 205/781
(58) Field of Classification Search ................. 204/431, 204/421, 424, 426, 280, 290.01, 290.1; 205/775, 205/780.5, 781
See application file for complete search history.

(56) References Cited

U.S. PATENT DOCUMENTS 5,037,525 A    8/1991   Badwal

FOREIGN PATENT DOCUMENTS

| JP | 63-501801   | 7/1988  |
| JP | 63-501801 T | 7/1988  |
| JP | 05-296971   | 11/1993 |

(Continued)

OTHER PUBLICATIONS

Nobuhito Imanaka et al., "Nitrogen Monoxide Gas Sensor Based on Solid Electrolytes With a Water-Insoluble Oxide Based Auxiliary Electrode", Electrochemical and Solid State Letters Col. 5, No. 11, Aug. 27, 2002, pp. H25-H26.

(Continued)

*Primary Examiner*—Alex Noguerola
*Assistant Examiner*—J. Christopher Ball
(74) *Attorney, Agent, or Firm*—Harness, Dickey & Pierce PLC

(57) ABSTRACT

The present invention uses a sensor electrode (3) in a nitrogen oxide sensor (10) which includes a nitrate or nitrite of an alkali metal and an oxide of a rare-earth element. The nitrate/nitrite of the alkali metal replaces part of the lattice of the oxide of the rare-earth element, forming a solid solution. The sensor electrode (3) therefore exhibits highly practical features, especially high water-insolubility and capability of nitrogen oxide measurement in a hot and humid atmosphere containing water vapor. Thus, a highly practical nitrogen oxide sensor electrode and nitrogen oxide sensor are provided which are usable in measurement in a hot and humid atmosphere containing water vapor.

21 Claims, 18 Drawing Sheets

FOREIGN PATENT DOCUMENTS

| | | | |
|---|---|---|---|
| JP | 2000-306426 | | 11/2000 |
| JP | 2001-133435 | * | 5/2001 |
| JP | 2001-194337 | * | 7/2001 |
| JP | 2003-042999 | | 2/2003 |

OTHER PUBLICATIONS

Atsushi Oda et al., "A New Solid Electrolytic Type Nitrogen Monoxide Gas Sensor With The Rare Earth Oxynitrate Based Auxiliary Electrode", The Electrochemical Society of Japan Dai 69 Kai Taikai Koen Yoshishu, Mar. 25, 1996, p. 44.

Japanese Patent Office Action and English translation thereof.

Atsushi Oda et al. "A New Solid Electrolyte Type Nitrogen Monoxide Gas Sensor with the Rare Earth Type Nitrogen Monoxide Gas Sensor with the Rare Earth Oxynitrate Based Auxiliary Electrode." Chemical Sensors, Apr. 1, 2002, vol. 18, Supplement A, p. 55-57 and full English translation thereof.

Atsushi Oda et al. "A New Solid Eletrolyte Type Nitrogen Monoxide Gas Sensor with the Rare Earth Oxide Based Auxiliary Electrode." *Kidorui (Rare Earth)*, May 16, 2002, No. 40, p. 232-233 and full English translation thereof.

Atsushi Oda et al. "A New Type of Nitrogen Monoxide Gas Sensor Applying Two Types of Solid Electrolyte with the Nitrate Based Auxiliary Electrode." Chemical Sensors, Dec. 4, 2001, vol. 17, Supplement B, p. 170-172.

* cited by examiner

DETECTING ELECTRODE AND NITROGEN OXIDE SENSOR USING THE SAME

TECHNICAL FIELD

The present invention relates in general to nitrogen oxide sensor electrodes and nitrogen oxide sensor incorporating such electrodes and in particular to, besides nitrogen oxides which are a sensor target, nitrogen oxide sensor electrodes and nitrogen oxide sensors which exhibit excellent responsiveness to nitrogen oxides in a humid atmosphere containing water vapor.

BACKGROUND ART

Nitrogen oxides, consisting mainly of nitrogen monoxide (NO) and nitrogen dioxide ($NO_2$), is a toxic gas. They are a major cause of acid rain and other kinds of acidic failings and one of seriously threatening factors to human health and environment. To restrict the amount of nitrogen oxides in the air, nitrogen oxide discharges from vehicles, various factories, etc. need to be brought under control. To this end, the amount of nitrogen oxide discharges from these sources must be placed under constant sensing, that is, monitoring.

In the event of, for example, a huge nitrogen oxide discharge caused by a certain malfunction of a nitrogen oxide source, such monitoring enables quick actions to be taken to prevent further nitrogen oxide leakage. This example illustrates how effective it is to sense/monitor the amount of nitrogen oxides discharged from sources to restrict their total amount in the air.

The sensing/monitoring of nitrogen oxide discharges from various sources requires compact, cheap, and easy-to-service nitrogen oxide sensors. The most promising of those sensors is one based on solid electrolyte in view of the desired capability, quick responsiveness, and quantitative sensing. This type of sensor is also suited to selective sensing of particular gases because a single type of ions migrate in a solid. Nitrogen oxide sensors are being suggested using various solid electrolytes.

Typically, nitrogen oxides are produced in combustion. So are heat and water vapor. Therefore, from a practical point of view, the solid electrolyte and sensor electrode used in a nitrogen oxide sensor need to be operational at high temperatures and impervious to water vapor. Thus, the desirable nitrogen oxide sensor electrode and nitrogen oxide sensor are capable of quick and quantitative sensing of nitrogen oxides in a humid atmosphere containing water vapor for practical purposes.

Since the sensor is expected to detect nitrogen oxide gases, its electrode needs to contain $NO^+$, $NO_2^-$, and $NO_3^-$ of nitrogen oxide origin.

However, the operational temperature of the nitrogen oxide sensor electrode, which conducts $NO^+$, should not exceed 200 degrees Celsius, restricting the sensor's applications. In addition, since both $NO_2^-$ and $NO_3^-$ are soluble in water, they are not suited to measurement in a humid atmosphere containing water vapor. For these reasons, there is no conventional nitrogen oxide sensor electrode that works well at high temperatures in an water-vapor-containing atmosphere.

Further, conventional solid electrolytes, which are soluble in water, cannot be used to detect nitrogen oxides in a humid atmosphere containing water vapor. This is another cause making it difficult to build an nitrogen oxide sensor usable in a water-vapor atmosphere for practical purposes.

Conceived to address these problems, the present invention has an objective to, especially, provide a highly water-insoluble, excellent practical performance nitrogen oxide sensor electrode, and a nitrogen oxide sensor incorporating such an electrode, which is useable for measurement in a high-temperature, humid atmosphere containing water vapor.

DISCLOSURE OF INVENTION

The sensor electrode of the present invention, to achieve the objective, is characterized by the inclusion of: a solid solution of a nitrate or nitrite of an alkali metal and an oxide of a rare-earth element.

With these features, a nitrogen oxide sensor electrode can be made which is suited to nitrogen oxide sensing, especially, in a hot and humid atmosphere containing water vapor. Specifically, the nitrate/nitrite replaces part of the lattice of the oxide, which is highly water-insoluble, thereby forming a solid solution. Thus, atmospheric water vapor is prevented from affecting $NO_2^-/NO_3^-$ in the nitrate/nitrite of the alkali metal. Nitrogen oxide sensing in a humid atmosphere thus becomes possible. In addition, nitrogen oxide sensing at high temperatures becomes possible.

For example, by incorporating that nitrogen oxide sensor electrode in a nitrogen oxide sensor, the sensor becomes capable of nitrogen oxide sensing in a not only in dry, but also humid atmosphere. The nitrogen oxide sensor thus made is highly practical: it works well at high temperatures and quickly and quantitatively sense nitrogen oxides without being affected by atmospheric water vapor. The nitrogen oxide sensor electrode is especially suitable for use in a nitrogen oxide sensor built around a solid electrolyte, imparting very good nitrogen oxide responsiveness to the nitrogen oxide sensor.

As to the sensor electrode of the present invention, the oxide of the rare-earth element is preferably $Eu_2O_3$, $Y_2O_3$ or $Gd_2O_3$. In addition, the nitrate/nitrite of the alkali metal is preferably a nitrite of an alkali metal, more preferably $KNO_2$.

With these features, a more practical nitrogen oxide sensor can be made which is usable at high temperatures and quickly and quantitatively senses nitrogen oxides without being affected by atmospheric water vapor.

The nitrogen oxide sensor in accordance with the present invention is characterized by the inclusion of: the foregoing nitrogen oxide sensor electrode, a solid electrolyte, and an oxide ion conductor. The sensor electrode and the oxide ion conductor are provided in contact with the surface of the solid electrolyte. The solid electrolyte conducts magnesium ions, aluminum ions, rare earth ions, zirconium ions, or hafnium ions.

With these features, the nitrogen oxide sensor is highly practical: it exhibits high water-insolubility and is suitable for measurement in a humid atmosphere containing water vapor.

Specifically, as the solid electrolyte, a conductor material for magnesium ions, aluminum ions, rare earth ions, zirconium ions, or hafnium ions is used. Thus, the solid electrolyte is highly water-insoluble. In addition, with the combined use of the nitrogen oxide sensor electrode and an oxide ion conductor, which is typically highly insoluble in water, the nitrogen oxide sensor exhibits high water-insolubility.

This ensures that atmospheric water vapor does not affect the sensing of nitrogen oxide concentrations in a humid atmosphere.

Hence, for example, the nitrogen oxide sensor is capable of sensing nitrogen oxides in vehicle exhaust emissions, which contain both nitrogen oxides and water vapor.

In addition, as the nitrogen oxide sensor in accordance with the present invention, it is preferred if the solid electrolyte is sandwiched between the nitrogen oxide sensor electrode and the oxide ion conductor.

The positioning of the solid electrolyte between the nitrogen oxide sensor electrode on the surface of the solid electrolyte and the oxide ions enables efficient nitrogen oxide sensing of cations moving in the solid electrolyte through the oxide ion conductor, improving nitrogen oxide sensing efficiency. This electrode-electrolyte-conductor structure is obtained for example by providing a sensor electrode on one side of a board-shaped solid electrolyte surface and providing an oxide ion conductor on the other side.

As to the nitrogen oxide sensor in accordance with the present invention, it is preferred if solid electrolyte has a Nasicon or β-iron sulfate crystal structure. The solid electrolyte is preferably a complex of $Mg_{1+X}Zr_4P_6O_{24+X}$ ($0<X\leq 0.4$) and $Zr_2O(PO_4)_2$; a solid solution, $Mg_{1-2Y}(Zr_{1-Y}Nb_Y)_4P_6O_{24}$ ($0\leq Y<1/2$), conducting magnesium ions; a composition, $(Al_{0.2}Zr_{0.8})_{20/19}Nb(PO_4)_3$, conducting aluminum ions; a composition, $R_{1/3}Zr_2(PO_4)_3$, conducting rare earth ions, where R is a rare earth atom; a composition, $ZrNb(PO_4)_3$, conducting zirconium ions; or a composition, $HfNb(PO_4)_3$, conducting hafnium ions.

As to the nitrogen oxide sensor in accordance with the present invention, it is preferred if the oxide ion conductor is made of at least one of the group consisting of fully stabilized zirconia, cerium oxide, bismuth oxide, hafnium oxide, thorium oxide, and lanthanum gallate.

These features better ensure that atmospheric water vapor does not affect the sensing of nitrogen oxide concentrations. Hence, the nitrogen oxide sensor is highly practical: it senses nitrogen oxides with good reproducibility in both dry and humid atmospheres.

Additional objects, advantages and novel features of the invention will be set forth in part in the description which follows, and in part will become apparent to those skilled in the art upon examination of the following or may be learned by practice of the invention.

BEST MODE FOR CARRYING OUT THE INVENTION

Figure 1:
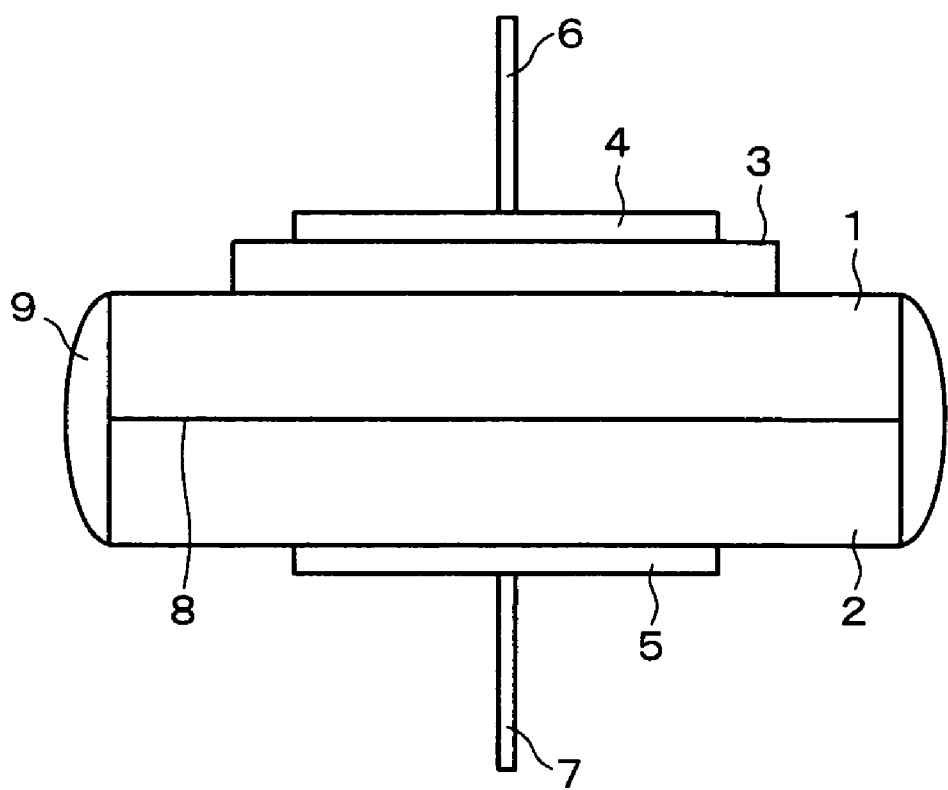
FIG. 1 is a schematic showing the arrangement of an example of the nitrogen oxide sensor in accordance with the present invention.

The following is a description of an embodiment of the present invention in reference to FIG. 1.

The nitrogen oxide sensor electrode of the present embodiment is made of a nitrate or nitrite of an alkali metal and an oxide of a rare-earth element. The sensor electrode is suitably used, especially, in nitrogen oxide sensors base on a solid electrolyte.

First, referring to FIG. 1, a nitrogen oxide sensor including the sensor electrode of the present embodiment will be described. As shown in the figure, a nitrogen oxide sensor 10 of the present embodiment includes: a solid electrolyte 1; an oxide ion conductor 2 provided in contact with the surface of the solid electrolyte 1; and a sensor electrode (nitrogen oxide sensor electrode) 3 provided on the surface of the solid electrolyte 1, but opposite the oxide ion conductor 2. In other words, the solid electrolyte 10 is located between the sensor electrode 3 and the oxide ion conductor. The solid electrolyte 1 and the oxide ion conductor 2 are joined using an inorganic adhesion agent 9.

On the surface of the sensor electrode 3 is there provided a gold net 4, opposite the solid electrolyte 1. On the surface of the oxide ion conductor 2 is there provided a platinum net 5, opposite the solid electrolyte 1. The these gold net 4 and the platinum net 5 are connected respectively to a gold line 6 and a platinum line 7. That is, the oxide ion conductor 2 is connected to the platinum line 7 through the platinum net 5. The sensor electrode 3 is connected to the gold line 6 through the gold net 4.

Next, the nitrogen oxide sensing mechanism of the nitrogen oxide sensor 10 will be described. When the nitrogen oxide sensor 10 is placed in an atmosphere containing nitrogen oxides, the sensor electrode 3 senses the nitrogen oxides in the atmosphere, causing movement of cations in the solid electrolyte 1.

At the interface 8 between the solid electrolyte 1 and the oxide ion conductor 2, the cations moving in the solid electrolyte 1 combine with the oxide ions having traveled through the oxide ion conductor 2 to the interface 8, forming stable oxides.

This phenomenon creates a force moving the cations, or ion drive force, through the solid electrolyte 1 in its thickness direction, that is, from the sensor electrode 3 side to the oxide ion conductor 2 side of the solid electrolyte 1. The drive force produces a potential difference between the gold net 4 and the platinum net 5. The potential difference has a magnitude in accordance with the nitrogen oxide concentration in the atmosphere, which can be measured across the gold line 6 and the platinum line 7.

More specifically, the electromotive force across the gold line 6 and the platinum line 7 is in proportion to the sensed nitrogen oxide concentration as mentioned above. Through the measurement of this electromotive force can the atmospheric nitrogen oxide concentration be measured.

Next, the structural members of the nitrogen oxide sensor 10 will be described.

The solid electrolyte 1 is preferably a conductor for magnesium ions, aluminum ions, rare earth ions, zirconium ions, or hafnium ions which has a Nasicon or β-iron sulfate crystal structure.

Here, "Nasicon" refers to a structural design of a crystal with a three-dimensional tunnel through which specific ionic species can readily move in the crystal. In other words, the design allows for movement of specific ionic species. The terminology came from $Na_{1+X}Zr_2P_{8-X}Si_XO_{12}$ (X≈2), or "Nasicon," which contains a sodium ion ($Na^+$) as a movable ionic species.

Similarly to the Nasicon crystal structure, the β-iron sulfate crystal structure also includes a three-dimensional tunnel through which specific ionic species can readily move in the crystal.

As the solid electrolyte 1 conducting sodium ions, specific examples include complexes of $Mg_{1+X}Zr_4P_6O_{24+X}$ (0<X≦0.4) and $Zr_2O(PO_4)_2$ and solid solutions of $Mg_{1-2Y}(Zr_{1-Y}Nb_Y)_4P_6O_{24}$ (0≦Y<1/2) compositions.

A complex of such a composition may be prepared by, for example, mixing $MgHPO_4 \cdot 3H_2O$, $ZrO(NO_3)_2 \cdot 2H_2O$, and $NH_4H_2PO_4$ in powder form at a predetermined ratio, then molding the powder mixture to give it a predetermined shape and size, and firing the molded mixture under predetermined conditions. The complex may however be prepared otherwise. The description hereafter on preparation methods for other materials are by no means limiting. The materials may be prepared by any other, non-described method.

The solid solution may be prepared by, for example, mixing $MgHPO_4 \cdot 3H_2O$, $ZrO(NO_3)_2 \cdot 2H_2O$, $Nb_2O_5$, and $NH_4H_2PO_4$ in powder form at a predetermined ratio and if necessary, firing the powder mixture. The obtained powder mixture is then molded to give it a predetermined shape and size, for example, pellets, and fired under predetermined conditions.

The solid electrolyte 1 conducting aluminum ions is exemplified by a composition, $(Al_{0.2}Zr_{0.8})_{20/19}Nb(PO_4)_3$.

Such a solid electrolyte may be prepared by mixing $Al(OH)_3$, $ZrO(NO_3)_2 \cdot 2H_2O$, $Nb_2O_5$, and $(NH_4)_2HPO_4$ at a predetermined ratio and if necessary, firing the powder mixture. The obtained powder mixture is then molded to give it a predetermined shape and size, for example, pellets, and fired under predetermined conditions.

Another example of the solid electrolyte 1 conducting aluminum ions is a composition, $Al_{1/3}Zr_2(PO_4)_3$. This particular solid electrolyte may be prepared by mixing $Al(OH)_3$ and $ZrO(NO_3)_2 \cdot 2H_2O$ at a predetermined ratio and if necessary, firing the powder mixture. The obtained powder mixture is then molded to give it a predetermined shape and size, for example, pellets, and fired under predetermined conditions.

The solid electrolyte 1 conducting rare earth ions is exemplified by a composition, $R_{1/3}Zr_2(PO_4)_3$ (R is a rare earth atom). A solid electrolyte of the composition, $R_{1/3}Zr_2(PO_4)_3$, may be prepared by mixing $R_2O_3$, $ZrO(NO_3)_2 \cdot 2H_2O$ and $(NH_4)_2HPO_4$ all in powder form at a predetermined ratio and if necessary, firing the powder mixture. The obtained powder mixture is then molded to give it a predetermined shape and size, for example, pellets, and fired under predetermined conditions. The rare earth atom represented by R in the formula is preferably scandium.

The solid electrolyte 1 conducting zirconium ions is exemplified by a composition, $ZrNb(PO_4)_3$. A solid electrolyte of the composition, $ZrNb(PO_4)_3$, may be prepared by mixing $ZrO_2$, $Nb_2O_5$ and $(NH_4)_2HPO_4$ all in powder form at a predetermined ratio and if necessary, firing the powder mixture. The powder mixture is then molded to give it a predetermined shape and size, for example, pellets, and fired under predetermined conditions.

The solid electrolyte 1 conducting hafnium ions is exemplified by a composition, $HfNb(PO_4)_3$. Such a solid electrolyte of the composition, $HfNb(PO_4)_3$, may be prepared by mixing $Hf(SO_4)_2$, $Nb_2O_5$ and $(NH_4)_2HPO_4$ all in powder form at a predetermined ratio and, if necessary, firing the powder mixture. The obtained powder mixture is then molded to give it a predetermined shape and size, for example, pellets, and fired under predetermined conditions.

The shape of the solid electrolyte 1 is determined as necessary and not limited in any particular manner. Examples are a disc and a rectangular flat board. A board shape with a substantially constant thickness is preferred. As shown in FIG. 1, the solid electrolyte 1 is of a disc shape in the present embodiment.

The thickness of the solid electrolyte 1 is preferably from 0.1 mm to 1.5 mm, more preferably less than 1.0 mm. These low thicknesses reduce internal resistance.

The part of the surface of the solid electrolyte 1 where it is in contact with the oxide ion conductor 2 is preferably from 10 mm² to 200 mm², more preferably from 50 mm² to 100 mm².

The oxide ion conductor 2 is not limited in any particular manner. The conductor 2 may be anything that allows for oxide ion movement. Preferred examples are fully stabilized zirconia, cerium oxide, bismuth oxide, hafnium oxide, thorium oxide, lanthanum gallate, and any of their combinations. In other words, the oxide ion conductor 2 may be composed of only one of these listed compounds or more than one of the compounds.

The shape of the oxide ion conductor 2, although determined in accordance with the solid electrolyte 1, is not limited in any particular manner. Examples are a disc and a rectangular flat board. As shown in FIG. 1, a board shape with a substantially constant thickness is preferred. The thickness of the oxide ion conductor 2 is preferably from 0.1 mm to 1.5 mm, more preferably less than 1.0 mm. These low thicknesses reduce internal resistance.

The part of the surface of the oxide ion conductor 2 where it is in contact with the solid electrolyte 1 is preferably from 10 $mm^2$ to 200 $mm^2$, more preferably from 50 $mm^2$ to 100 $mm^2$.

The sensor electrode 3 contains a solid solution of either a nitrate or nitrite of an alkali metal and an oxide of a rare-earth element. Used with the oxide of the rare-earth element, the nitrate/nitrite of the alkali metal replaces part of the lattice of the oxide, forming a solid solution. Thus, the sensor electrode 3 exhibits high water-insolubility, making it possible to install the nitrogen oxide sensor 10, incorporating the sensor electrode 3, in a humid atmosphere containing water vapor. The sensor 10 is thus rendered highly practical. The oxide of the rare-earth element is preferably $Eu_2O_3$, $Y_2O_3$, or $Gd_2O_3$. The nitrite of the alkali metal is preferably $KNO_2$.

The sensor electrode 3 is specified where necessary, similarly to the solid electrolyte 1. Although not limited in any particular manner, the electrode 3 may be, for example, of a disc or rectangular flat board shape. In the case of a board shape, the thickness of the sensor electrode 3 is preferably from 0.1 mm to 1.0 mm, more preferably from 0.5 mm to 0.8 mm.

The part of the surface of the sensor electrode 3 where it is in contact with the solid electrolyte 1 is preferably from 10 $mm^2$ to 200 $mm^2$, more preferably from 10 $mm^2$ to 30 $mm^2$. The solid electrolyte 1 side of the sensor electrode 3 is preferably from 80% to 120%, more preferably from 90% to 110%, of the sensor electrode 3 side of the solid electrolyte 1.

To achieve good responsiveness of the sensor electrode 3, it is preferred if the nitrite and the rare earth oxide are well mixed to form a solid, e.g., a solid solution. For this purpose, it is expected that rare-earth element oxides with a large ion radius are ready to form a solid solution with a nitrite.

Therefore, among rare-earth element oxides, oxides of Sm, Eu, Gd are prospective candidates.

In addition, the nitrogen oxide sensor 10 in accordance with the present invention is capable of detecting nitrogen oxides in a water-vapor atmosphere and at high temperatures with excellent reproducibility. This is because of the heat- and water-resistance of the rare-earth element oxide and the good formation of a solid (solid solution) made of the rare-earth element oxide and the alkali metal nitrite.

EXAMPLES

Next, the present invention will be described in further detail through examples. The invention is however by no means limited by these examples.

Example 1

The following will describe a nitrogen oxide sensor which is an example of the present invention, as well as the solid electrolyte, the oxide ion conductor, and the sensor electrode, in reference to FIG. 1 to FIG. 7.

Solid Electrolyte

The nitrogen oxide sensor of the present example is constructed as shown in the schematic of FIG. 1. A solid electrolyte 1 which was a component of the nitrogen oxide sensor 10 of the present example was fabricated as follows: $Al(OH)_3$, $ZrO(NO_3)_2 \cdot 2H_2O$, $Nb_2O_5$, and $(NH_4)_2HPO_4$ in powder form was mixed at a molar ratio of $Al(OH)_3:ZrO(NO_3)_2 \cdot 2H_2O:Nb_2O_5:(NH_4)_2HPO_4 = 8:32:19:114$. The mixture was heated in the air up to 1000 degrees Celsius and then at that temperature for 12 hours. After the heating, the mixture was crushed to form pellets and heated in the air at 1200 degrees Celsius for 12 hours and subsequently at 1300 degrees Celsius for 12 hours.

The pellets mixture thus heated was crush again and sintered through heating in the air at 1300 degrees Celsius for 12 hours. Thus, $(Al_{0.2}Zr_{0.8})_{20/19}Nb(PO_4)_3$, as the solid electrolyte 1 of a disc shape, was prepared which conducted aluminum ions ($Al^{3+}$). The solid electrolyte 1 was 1.0 mm thick. The part of its surface where it is in contact with the oxide ion conductor 2 was 95 $mm^2$. So was that where it is in contact with the sensor electrode 3.

Oxide Ion Conductor

An oxide ion conductor 2 which was a component of the nitrogen oxide sensor 10 of the present example was fabricated as follows: $ZrO_2$ and $Y_2O_3$ in powder form was mixed at a molar ratio of $ZrO_2:Y_2O_3=9:1$. The mixture was fired in the air at 1600 degrees Celsius for 12 hours. The firing process was carried out twice. Thus, $(ZrO_2)_{0.9}(Y_2O_3)_{0.1}$, as the oxide ion conductor 2 of a disc shape, was prepared which was made up of fully stabilized zirconia. The oxide ion conductor 2 was 1.0 mm thick. The part of its surface where it is in contact with the solid electrolyte 1 was 95 $mm^2$. That is, in the present example, the oxide ion conductor 2 was made in the same shape as the solid electrolyte 1. $(ZrO_2)_{0.9}(Y_2O_3)_{0.1}$ will be abbreviated as YSZ.

Sensor Electrode

A sensor electrode 3 which was a component of the nitrogen oxide sensor 10 of the present example was fabricated as follows: Europium oxide $Eu_2O_3$ and potassium nitrite $KNO_2$ in powder form were mixed at a molar ratio of $Eu_2O_3:KNO_2=2:1$. The mixture was mixed in the air for 12 hours using a ball mill. The powder mixture thus mixed was then molded to form pellets and sintered through heating at 450 degrees Celsius for 12 hours. Thus, the sensor electrode 3 was obtained.

Figure 2:
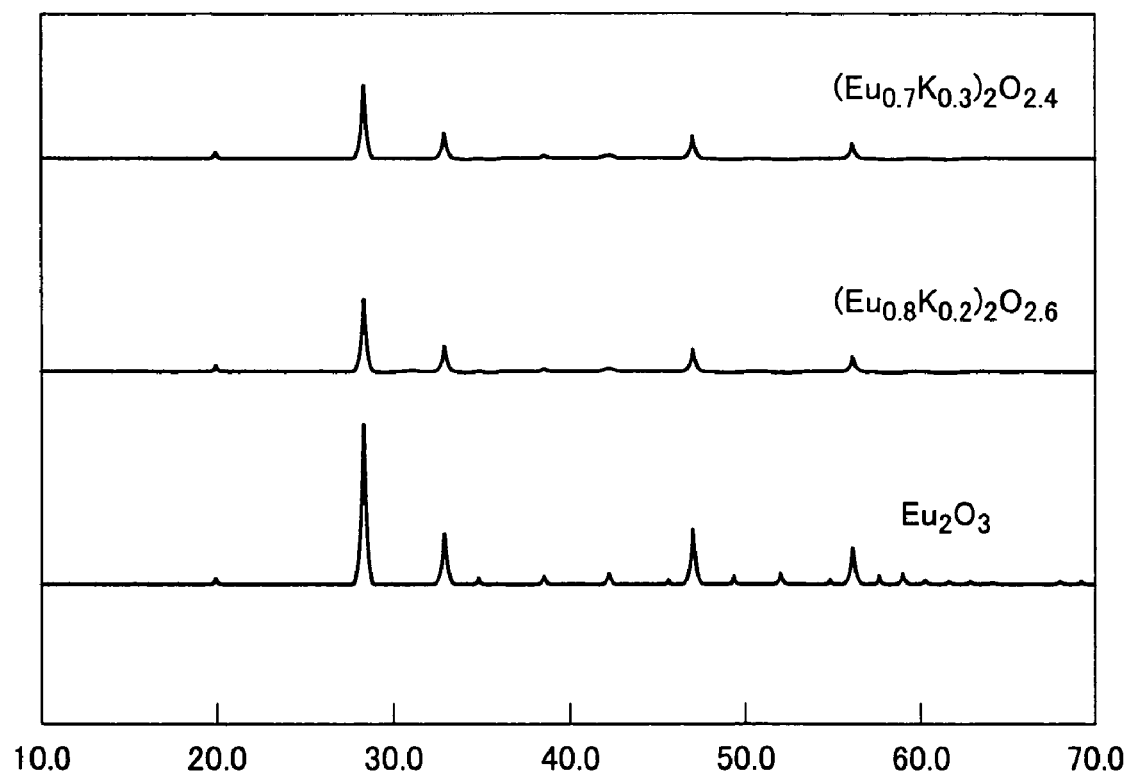
FIG. 2 is a spectrum diagram showing results of the X-ray diffraction of powder making up a sensor electrode of example 1.

The sensor electrode 3 thus fabricated was subjected to X-ray diffraction for measurement of the powder (X-ray diffractionmetry, or XRD). Results are shown in FIG. 2.

Referring to the figure, the X-ray crystal diffraction for the sensor electrode 3 detected a single peak, which indicated $Eu_2O_3$. A peak shift was confirmed. In other words, the figure showed changes in the lattice size caused by K replacing some of Eu, which in turn showed that $Eu_2O_3$ and $KNO_2$ had formed a solid solution.

Replacing Eu with K changes the lattice size because of the size difference between these elements. In the figure, $(Eu_{0.8}K_{0.2})_2O_{2.6}$ indicates $Eu_2O_3+0.2KNO_2$. $(Eu_{0.7}K_{0.3})_2O_{2.4}$ indicates $Eu_2O_3+0.3KNO_2$.

Nitrogen Oxide Sensor

The solid electrolyte 1 and oxide ion conductor 2 thus fabricated were stacked as shown in FIG. 1. The side face was covered with an inorganic adhesion agent 9 to seal out the interface 8 between the solid electrolyte 1 and the oxide ion conductor 2 from the external atmosphere. In the present example, Sumiceram 17D (product name; manufactured by Asahi Chemical Co., Ltd.) was used as the inorganic adhesion agent 9.

The sensor electrode 3 was then stacked onto the disc-shape solid electrolyte 1 which conducts aluminum ions $Al^{3+}$, so that the former comes in contact with the surface of the latter. The two were then fixed to each other. A gold net 4 and a gold line 6 were provided as shown in FIG. 1 which would be the electrode and lead line on the sensor electrode 3 side of the solid electrolyte 1. A platinum net 5 and a platinum line 7 were also provided which would be the electrode and lead line on the oxide ion conductor 2 side of the solid electrolyte 1, which completes the fabrication of the nitrogen oxide sensor 10 of the present example.

Conditions in Nitrogen Oxide Measurement

Samples were prepared for nitrogen oxide measurement. The samples were prepared by mixing 1% $N_2$-diluted NO with air, with the NO concentration as the nitrogen oxide being varied between 200 ppm and 2000 ppm. This NO concentration range equates that in vehicle exhaust emissions which are a common nitrogen oxide source.

The measurement temperature was set to 450 degrees Celsius. The total flow of the measurement sample (gas) was maintained at 100 ml/minute so that the oxygen concentration in the measurement sample would be always 20 wt. %. The output of the nitrogen oxide sensor 10 was measured using an electrometer, R8240, manufactured by Advantest Corp.

Preparation of Measurement Sample Containing Water Vapor

A measurement sample containing 4.87 g/m³ water vapor was prepared by passing 1% $N_2$-diluted NO through deionized water so that the latter would bubble and mix with the former. During the bubbling, the latter was placed in a triangle flask in a thermostatic bath which was regulated at 25 degrees Celsius.

Sensing Principles

The following depicts the sensing principles of the nitrogen oxide sensor 10 of the present example fabricated in the foregoing manner, specifically, the reactions likely to be taking place in the sensor electrode 3, at the interface between the sensor electrode 3 and the solid electrolyte 1, at the interface 8 between the oxide ion conductor 2 and the solid electrolyte 1, and in the reference electrode.

Sensor Electrode

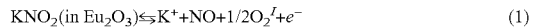

$$KNO_2(in\ Eu_2O_3) \leftrightarrows K^+ + NO + 1/2O_2^I + e^- \quad (1)$$

Sensor Electrode/Solid Electrolyte Interface

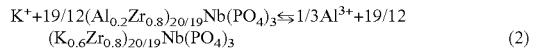

$$K^+ + 19/12(Al_{0.2}Zr_{0.8})_{20/19}Nb(PO_4)_3 \leftrightarrows 1/3Al^{3+} + 19/12(K_{0.6}Zr_{0.8})_{20/19}Nb(PO_4)_3 \quad (2)$$

Oxide Ion Conductor/Solid Electrolyte Interface

$$1/3Al^{3+} + 1/2O^{2-} \leftrightarrows 1/6Al_2O_3 \quad (3)$$

Reference Electrode

$$1/4O_2^{II} + e^- \leftrightarrows 1/2O^{2-} \quad (4)$$

The net reaction in the nitrogen oxide sensor 10 is given by equation (5):

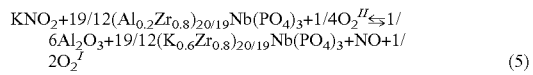

$$KNO_2 + 19/12(Al_{0.2}Zr_{0.8})_{20/19}Nb(PO_4)_3 + 1/4O_2^{II} \leftrightarrows 1/6Al_2O_3 + 19/12(K_{0.6}Zr_{0.8})_{20/19}Nb(PO_4)_3 + NO + 1/2O_2^I \quad (5)$$

Hence, based on the Nernst equation, the electromotive force E appearing between the gold line 6 and platinum line 7 on the nitrogen oxide sensor 10 is given by equation (6):

$$E = E_0 - (R/nF)T\ln\{(aAl_2O_3)^{1/6}(a(K_{0.6}Zr_{0.8})_{20/19}Nb(PO_4)_3)^{19/12}(P_{NO})(P_{O_2}^I)^{1/2}(aKNO_2)^{-1}(a(Al_{0.2}Zr_{0.8})_{20/19}Nb(PO_4)_3)^{-19/12}(P_{O_2}^{II})^{-1/4}\}$$
$$(E_0 = \text{constant number}, n=1.00) \quad (6)$$

where R is the gas constant, F is the Faraday's constant, T is the absolute temperature, a is an activity, and P is a partial pressure.

As mentioned earlier, the oxygen concentration in the measurement sample is regulated at a constant value of 20 wt. %. Therefore, $O_2^I$ and $O_2^{II}$ have an equal partial pressure of 2.1 Pa×10⁴ Pa (indicated by $PO_2^I$ and $PO_2^{II}$ respectively). So, there is no effect of oxygen's partial pressure. Since the activity of a solid is constant, equation (6) giving the electromotive force E of the nitrogen oxide sensor 10 can be rearranged to simple equation (7):

$$E = E_0' - (R/nF)T\ln(P_{NO})(n=1.0)\ (E_0' = \text{constant number}, n=1.00) \quad (7)$$

Evaluation of Nitrogen Oxide Sensor

The response of the nitrogen oxide sensor 10 to NO gases (200 ppm to 2000 ppm) was measured at 450 degrees Celsius under conditions detailed above. Results are shown in FIGS. 3 to 7.

Sensing in Dry Atmosphere

Figure 3:
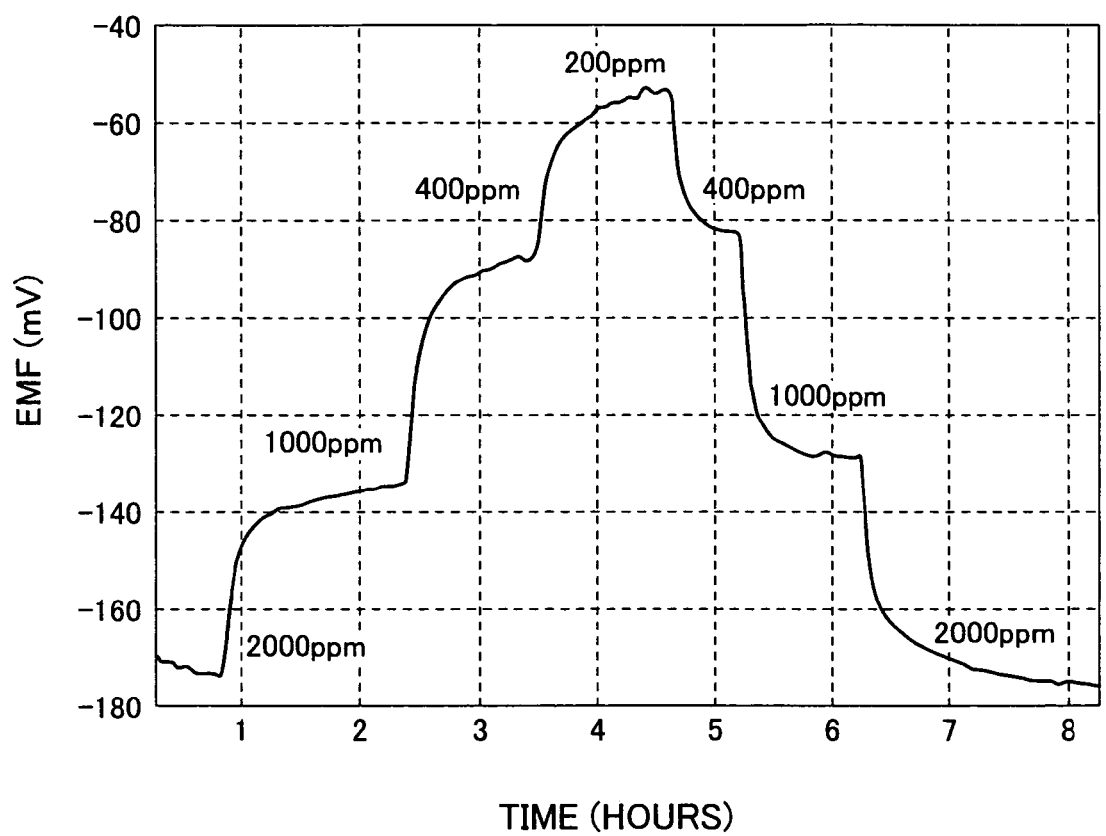
FIG. 3 is a graph of a response curve representing the electromotive force of an example 1 nitrogen oxide sensor induced by a NO gas contained in a dry measurement sample.

FIG. 3 is a response curve representing the electromotive force of the nitrogen oxide sensor 10 induced by NO gases in dry measurement samples. The response curve in the figure was observed when the NO gas concentration was varied between 200 and 2000 ppm. The figure indicates that the electromotive force (output) of the nitrogen oxide sensor 10 in a dry atmosphere monotonically increased with a decrease in the NO gas concentration and monotonically decreased with an increase in the NO gas concentration. Further, the figure indicates that the response reached 90% of the full response level within 10 minutes. It would be understood that the reactions in the nitrogen oxide sensor 10 were quick, continuous, and highly reproducible, which translated into the good response of the nitrogen oxide sensor 10.

Figure 4:
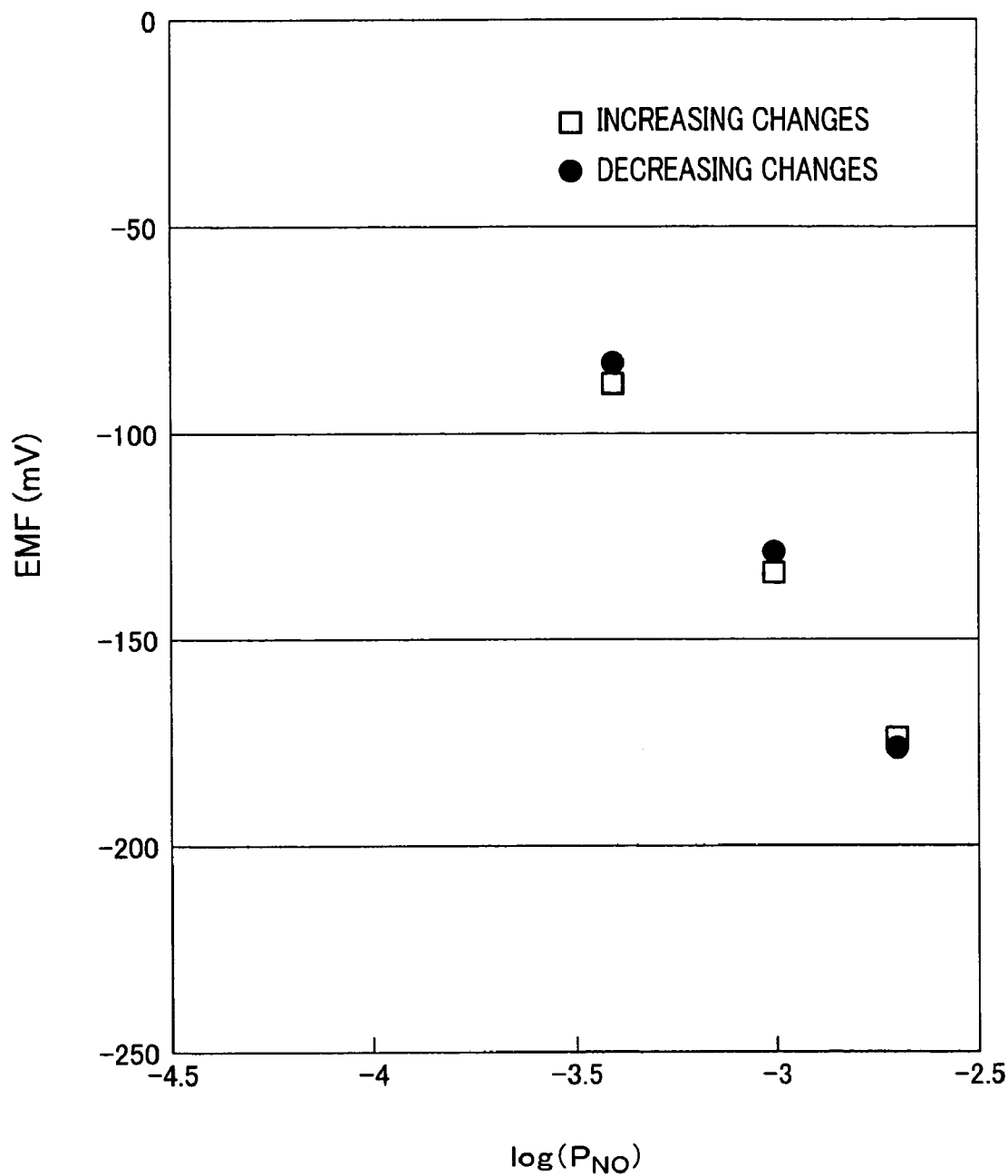
FIG. 4 is a graph showing the electromotive force of example 1 nitrogen oxide sensor induced by a NO gas contained in a dry measurement sample as in FIG. 3, with the NO gas concentration being varied both in increasing/decreasing directions.

Now, moving to FIG. 4, it would be understood that the response of the nitrogen oxide sensor 10 is reversible, because the electromotive force assumed reproducible values both in cases where the NO gas concentration increased (white squares) and where it decreased (black circles).

Sensing in Humid Atmosphere

Figure 5:
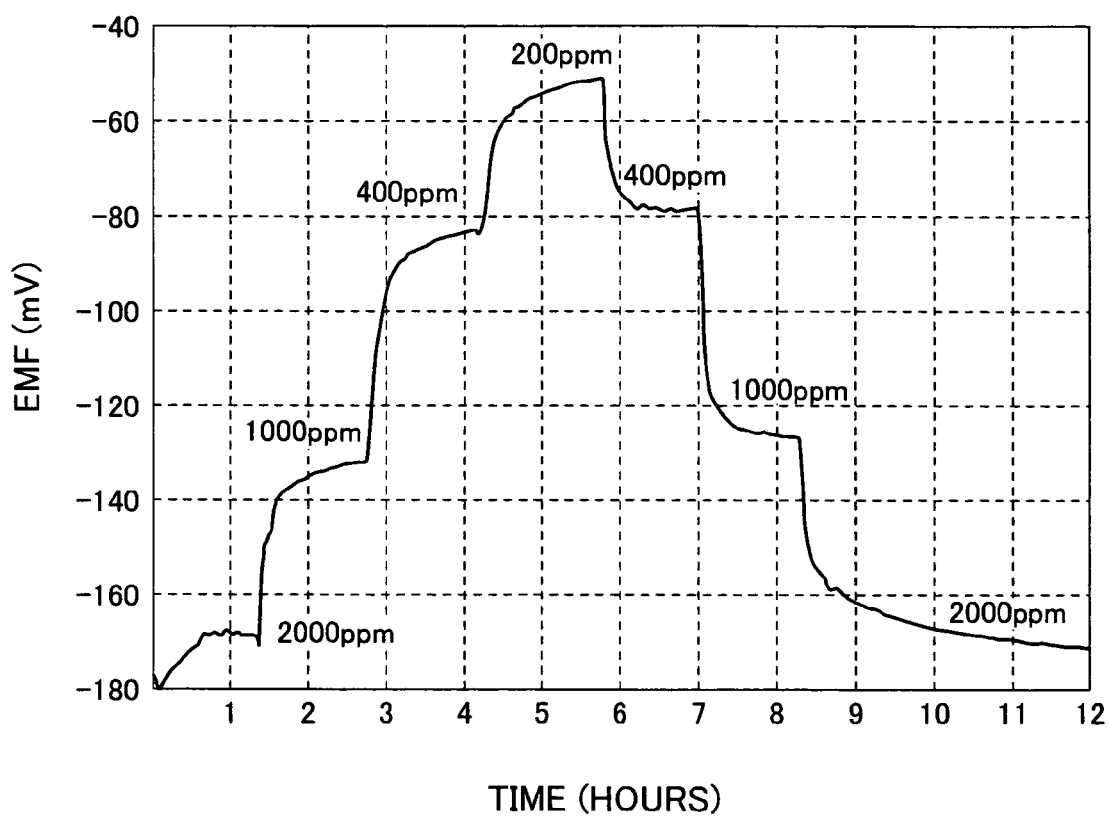
FIG. 5 is a graph of a response curve representing the electromotive force of example 1 nitrogen oxide sensor induced by a NO gas contained in a water-vapor humid measurement sample.

FIG. 5 is a response curve representing the electromotive force of the nitrogen oxide sensor 10 induced by NO gases in water-vapor humid measurement samples. As shown in the figure, the electromotive force (output) of the nitrogen oxide sensor 10 in a humid atmosphere containing water vapor monotonically increased with a decrease in the NO gas concentration and monotonically decrease with an increase in the NO gas concentration. The figure also indicates that the response reached 90% of the full response level within 10 minutes, similarly to the sensing in a dry atmosphere. It would be understood that the response was quick, continuous, and highly reproducible.

Figure 6:
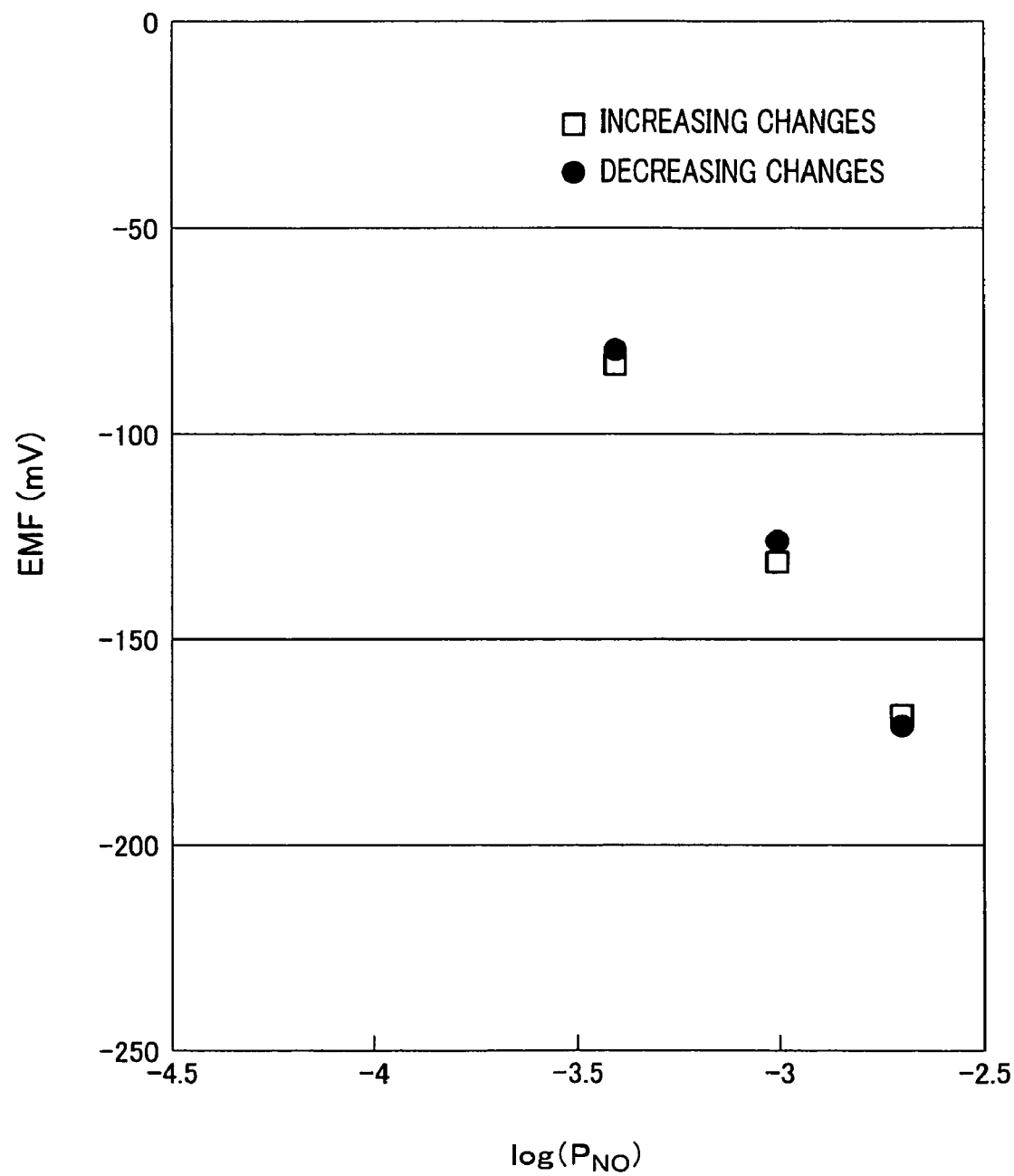
FIG. 6 is a graph showing the electromotive force of example 1 nitrogen oxide sensor induced by a NO gas contained in a humid measurement sample as in FIG. 5, with the NO gas concentration being varied both in increasing/decreasing directions.

Referring to FIG. 6, the response of the nitrogen oxide sensor 10 is reversible again in a humid atmosphere, similarly to a dry atmosphere, because the electromotive force assumed reproducible values both in cases where the NO gas concentration increased (white squares) and where it decreased (black circles).

Comparison of Dry/Humid Atmosphere

Figure 7:
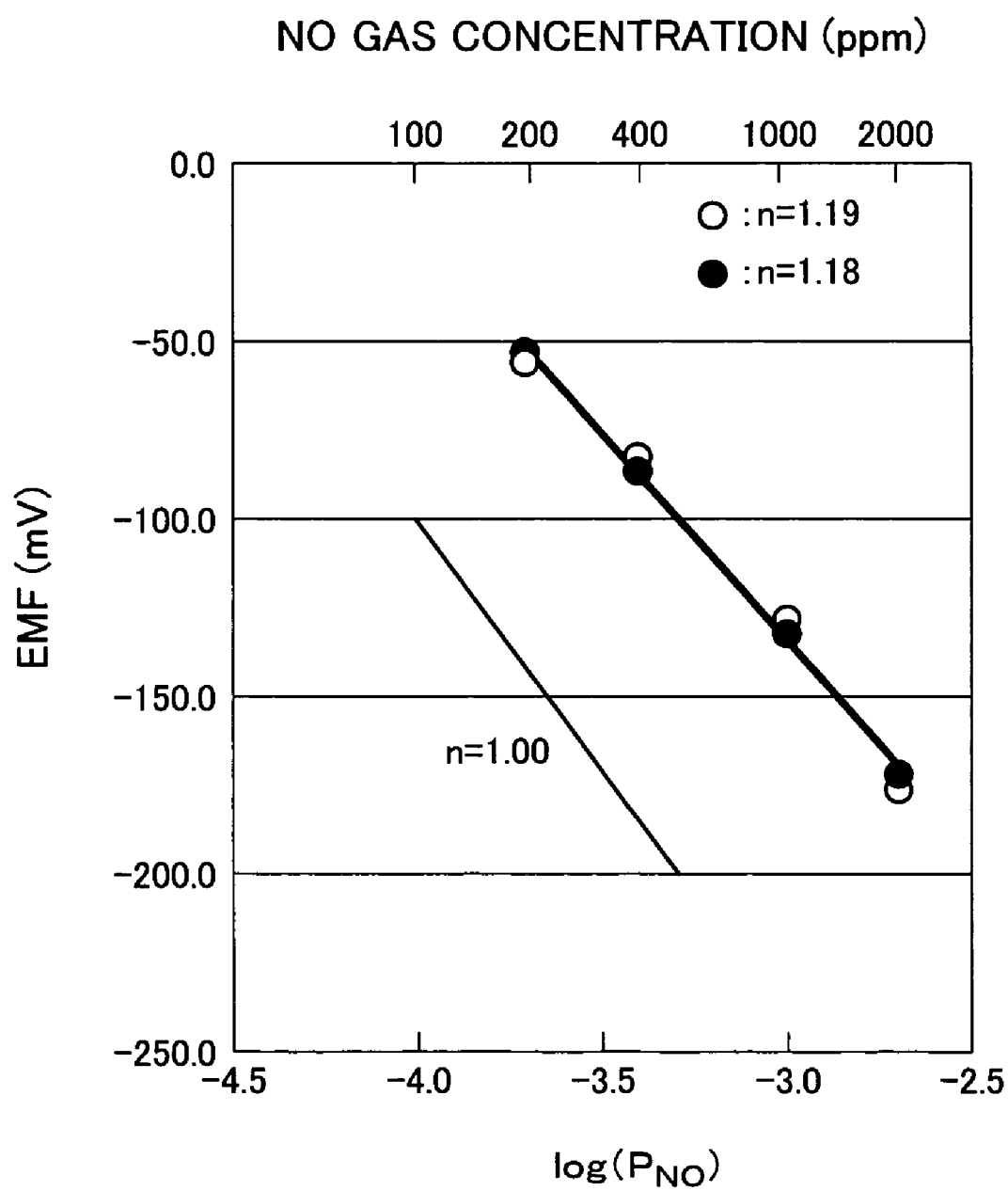
FIG. 7 is a graph showing NO gas concentration dependence of the electromotive force of example 1 nitrogen oxide sensor for the FIG. 4 dry case and the FIG. 6 humid case.

FIG. 7 depicts the relationship between (i) the relationship between the electromotive force and the NO gas concentration in the dry measurement sample in FIG. 4, (ii) the relationship between the electromotive force and the NO gas concentration in the humid measurement sample in FIG. 6, and (iii) the electromotive force and the NO gas concentration calculated from equation (7). Referring to the figure, the measurements on dry samples (white circles) and the measurements on humid samples (black circles) both exhibit a one-to-one correspondence between the electromotive forces of the nitrogen oxide sensor 10 and the logarithms of the NO gas concentrations.

In addition, the measurements on dry and humid samples are equal throughout the concentration range. The nitrogen oxide sensor 10 is highly practical for its ability to sense NO gas without being affected by the water vapor in the samples. This is probably because water-soluble $KNO_2$, which is involved in the response of the nitrogen oxide sensor 10, replaced part of the lattice of highly water-resistant $Eu_2O_3$, forming a solid solution.

Still referring to FIG. 7, electromotive forces were plotted against NO gas concentrations for both dry and humid samples, so as to determine the number of electrons transferred in the reaction, assigned n, in equation (7). Results showed n=1.19 for dry samples and n=1.18 for humid samples. Both values are very near the theoretical number of electrons transferred in the reaction (n=1.00) calculated from equation (7). It is therefore understood that theoretical reactions, as in equations (1) to (7), were taking place in the nitrogen oxide sensor 10 both for dry and humid samples.

As in the foregoing, the electromotive force of the nitrogen oxide sensor 10, which is built around the combination of the solid electrolyte 1 conducting trivalent aluminum cations, the oxide ion conductor 2 conducting divalent oxide anions, and the sensor electrode 3 made up of highly water-insoluble oxides, complies with the Nernst equation. The reactions in the nitrogen oxide sensor 10 are quick, continuous, and highly reproducible.

In addition, the nitrogen oxide sensor 10 demonstrates high sensing capability not only in a dry atmosphere, but also a hot and humid atmosphere. Therefore, the sensor electrode 3 and the nitrogen oxide sensor 10 are both highly practical and suited to the detection of nitrogen oxides produced together with water vapor in combustion.

Example 2

The following will describe a nitrogen oxide sensor which is another example of the present invention, as well as the solid electrolyte, the oxide ion conductor, and the sensor electrode, in reference to FIG. 1 and FIG. 8 to FIG. 10.

Solid Electrolyte and Oxide Ion Conductor

The nitrogen oxide sensor of the present example is constructed as shown in the schematic of FIG. 1. The solid electrolyte 1 and the oxide ion conductor 2, which were components of the nitrogen oxide sensor 10 of the present example, were fabricated identically to example 1.

Sensor Electrode

The sensor electrode 3, which was a component of the nitrogen oxide sensor 10 of the present example, was fabricated identically to example 1, except that the europium oxide $Eu_2O_3$ in example 1 was replaced with yttrium oxide $Y_2O_3$.

Figure 8:
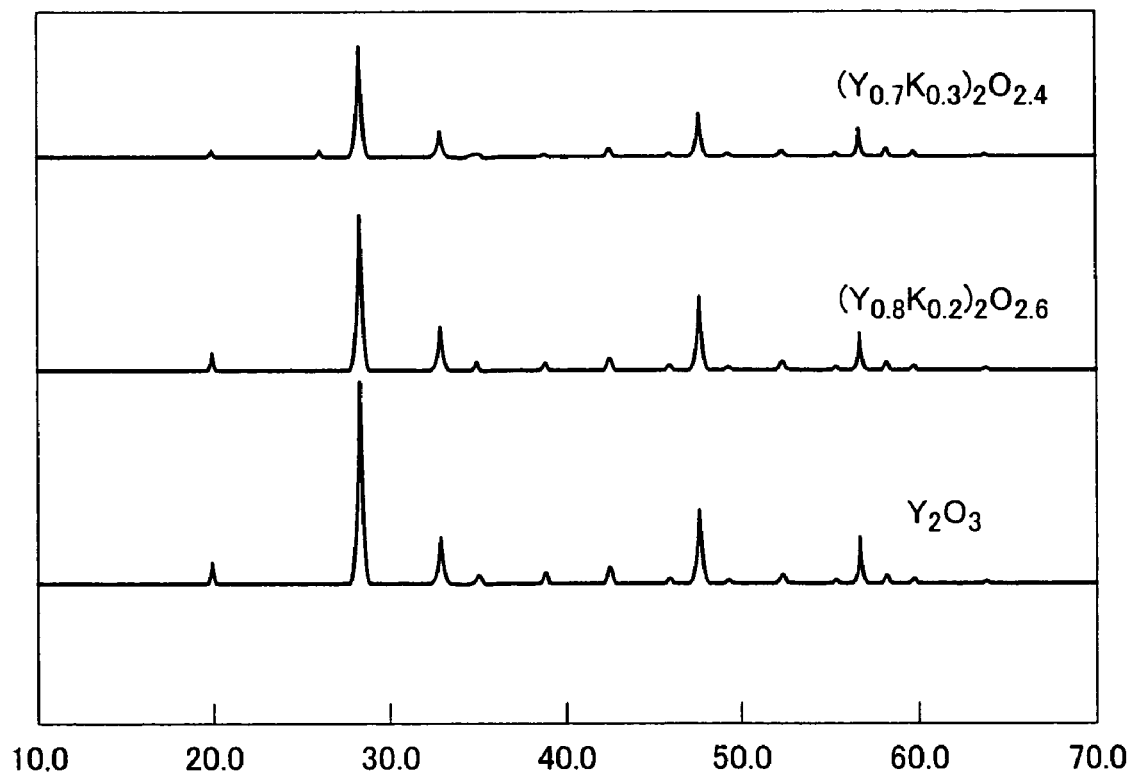
FIG. 8 is a spectrum diagram showing results of the X-ray diffraction of powder making up a sensor electrode of example 2.

The sensor electrode 3 thus fabricated was subjected to X-ray diffraction for measurement of the powder (X-ray diffractionmetry, or XRD). Results are shown in FIG. 8.

Referring to the figure, the X-ray crystal diffraction for the sensor electrode 3 sample detected a single peak, which indicated $Y_2O_3$. A peak shift was confirmed. This shows that $KNO_2$ replaced part of the lattice of $Y_2O_3$, forming a solid solution. In the figure, $(Y_{0.8}K_{0.2})_2O_{2.6}$ indicates $Y_2O_3$+ $0.2KNO_2$. $(Y_{0.7}K_{0.3})_2O_{2.4}$ indicates $Y_2O_3+0.3KNO_2$.

Nitrogen Oxide Sensor

As mentioned earlier, the nitrogen oxide sensor 10 of the present example was fabricated identically to example 1, except that yttrium oxide $Y_2O_3$ was used in place of europium oxide $Eu_2O_3$ in the fabrication of the sensor electrode 3.

Conditions in Nitrogen Oxide Measurement

Nitrogen oxide measurement was conducted identically to example 1.

Sensing Principles

As mentioned earlier, the nitrogen oxide sensor 10 of the present example was identical to example 1, except that yttrium oxide $Y_2O_3$ was used in place of europium oxide $Eu_2O_3$ to fabricate the sensor electrode 3.

Therefore, it would be safe to assume that the same reactions as in equations (1) to (7) discussed in example 1 took place except that $Eu_2O_3$ is replaced by $Y_2O_3$ in equation (1).

Sensing in Dry Atmosphere

Figure 9:
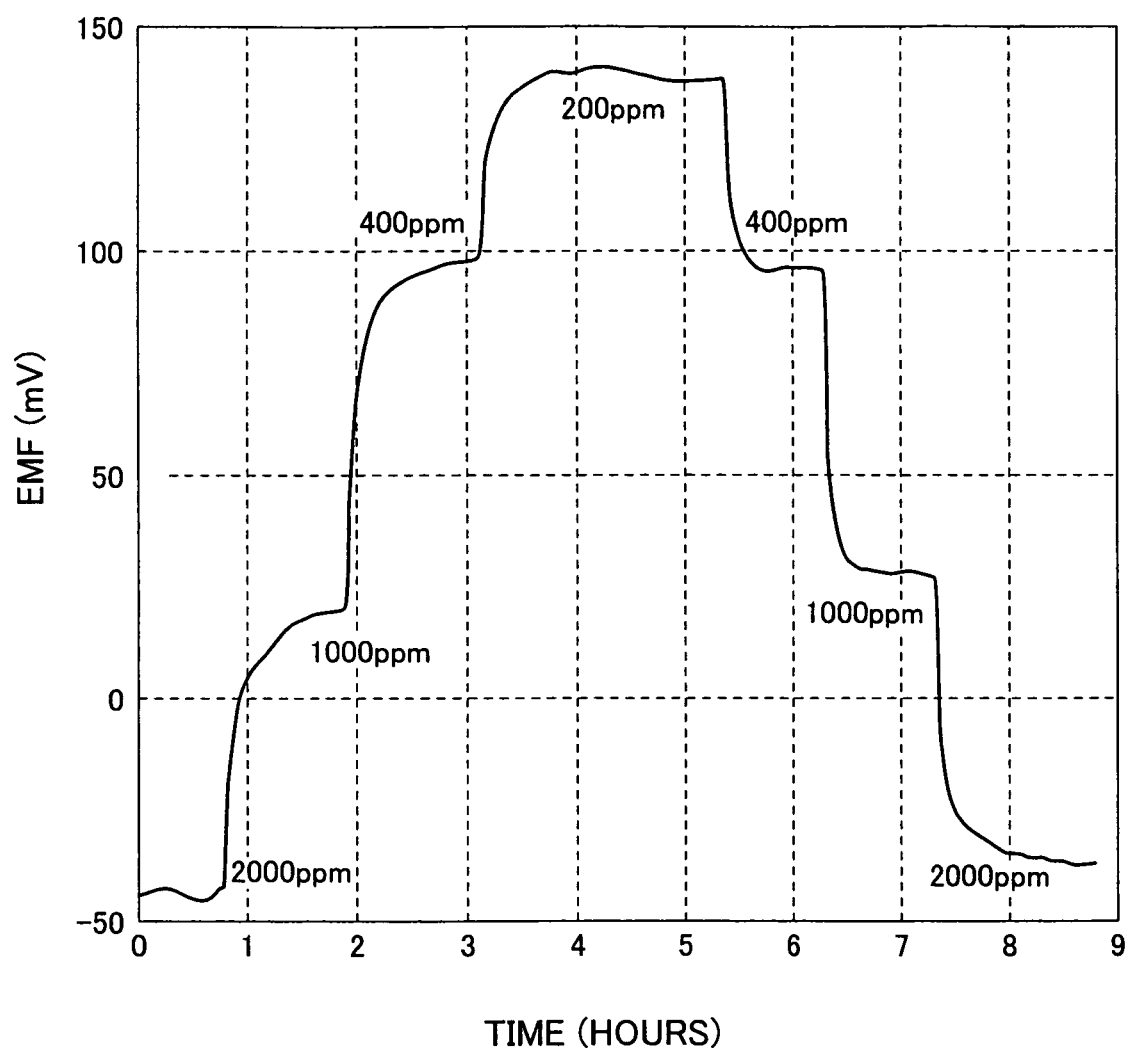
FIG. 9 is a graph of a response curve representing the electromotive force of an example 2 nitrogen oxide sensor induced by a NO gas contained in a dry measurement sample.

FIG. 9 is a response curve representing the electromotive force of the nitrogen oxide sensor 10 induced by the NO gas contained in dry measurement samples. As shown in the figure, The electromotive force (output) of the nitrogen oxide sensor 10 in a dry atmosphere monotonically increased with a decrease in the NO gas concentration and monotonically decreased with an increase in the NO gas concentration.

Figure 10:
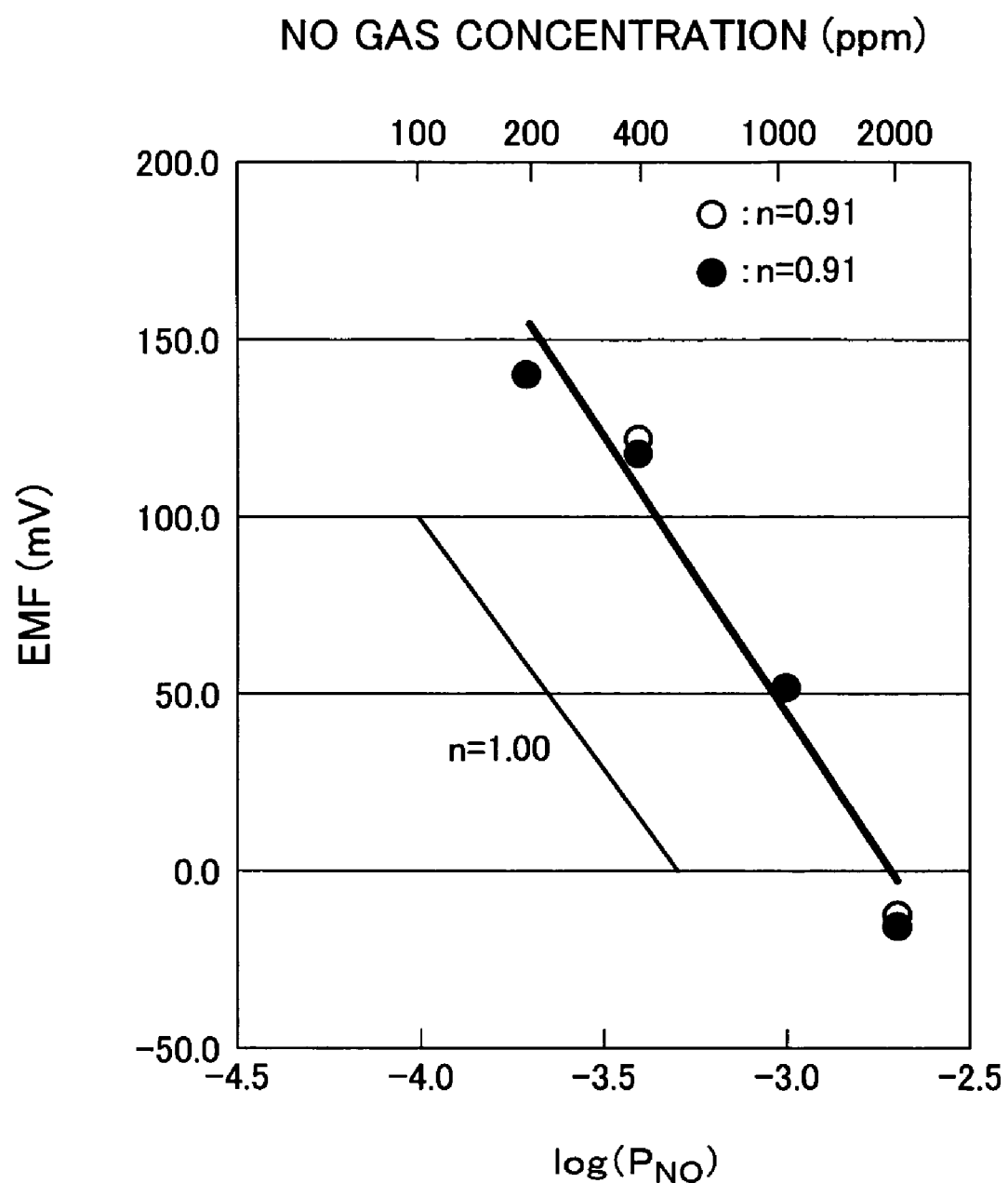
FIG. 10 is a graph showing the electromotive force of the example 2 nitrogen oxide sensor induced by a NO gas contained in a dry measurement sample as in FIG. 9, with the NO gas concentration being varied both in increasing/decreasing directions.

Referring to FIG. 10, the reactions in the nitrogen oxide sensor 10 are reversible, because the electromotive force assumed reproducible values both in cases where the NO gas concentration increased (white circles) and where it decreased (black circles).

Still referring to the figure, electromotive forces were plotted against NO gas concentrations for dry samples, so as to determine the number of electrons transferred in the reaction, assigned n, in equation (7). Results showed n=0.91 for both increasing and decreasing NO gas concentrations. Both values are very near the theoretical number of electrons transferred in the reaction (n=1.00) calculated from equation (7). It is therefore understood that theoretical reactions were taking place in the nitrogen oxide sensor 10 both for dry and humid samples.

Example 3

Figure 11:
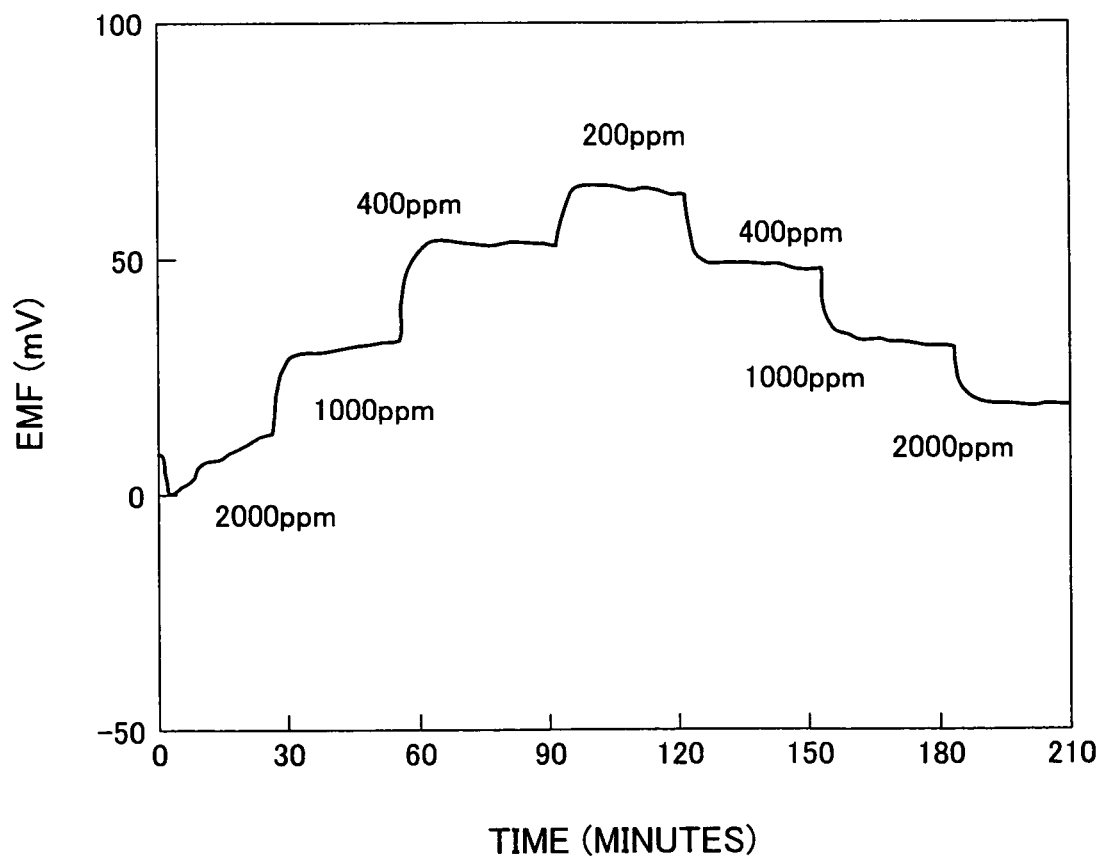
FIG. 11 is a graph of a response curve representing the electromotive force of an example 3 nitrogen oxide sensor induced by a NO gas contained in a dry measurement sample.
Figure 12:
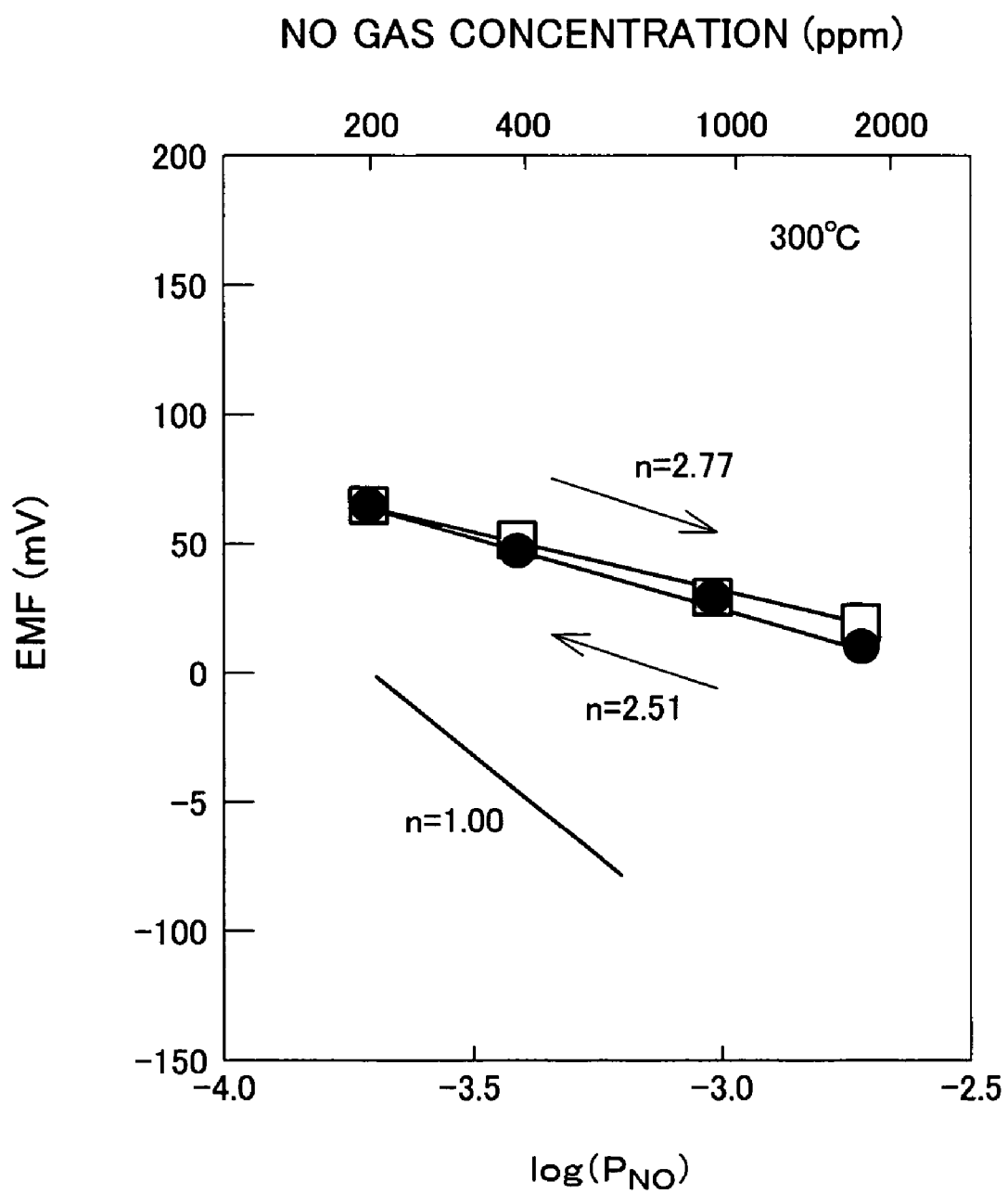
FIG. 12 is a graph showing the electromotive force of the example 3 nitrogen oxide sensor induced by a NO gas contained in a dry measurement sample as in FIG. 11, with the NO gas concentration being varied both in increasing/decreasing directions.

The following will describe a nitrogen oxide sensor which is another example of the present invention, as well as the solid electrolyte, the oxide ion conductor, and the sensor electrode, in reference to FIG. 1 and FIG. 11 to FIG. 12. Note that in the present example, $0.35Gd_2O_3$-$0.3LiNO_3$, which showed a maximum permittivity for $(1-x)/2Gd_2O_3$-$xLiNO_3$, was used as the sensor electrode; $(Al_{0.2}Zr_{0.8})_{20/19}Nb(PO_4)_3$ as the solid electrolyte (multivalent cation conductor) similarly to example 1; and $(ZrO_2)_{0.92}(Y_2O_3)_{0.08}$ as the oxide ion conductor.

Solid Electrolyte and Oxide Ion Conductor

The nitrogen oxide sensor of the present example is constructed as shown in the schematic of FIG. 1. The solid electrolyte 1 and the oxide ion conductor 2, which were components of the nitrogen oxide sensor 10 of the present example, were fabricated identically to example 1.

Sensor Electrode

The sensor electrode 3, which was a component of the nitrogen oxide sensor 10 of the present example, was fabricated identically to example 0.1, except that the europium oxide $Eu_2O_3$ in example 1 was replaced with gadolinium oxide $Gd_2O_3$.

Nitrogen Oxide Sensor

The nitrogen oxide sensor 10 of the present example, as mentioned earlier, was fabricated identically to example 1, except that gadolinium oxide $Gd_2O_3$ and lithium nitrate $LiNO_3$ were used in place of europium oxide $Eu_2O_3$ and potassium nitrite $KNO_2$ respectively at $Gd_2O_3:LiNO_3=0.35:0.3$ in the fabrication of the sensor electrode 3.

Conditions in Nitrogen Oxide Measurement

Nitrogen oxide measurement was conducted identically to example 1.

Sensing Principles

As mentioned earlier, the nitrogen oxide sensor 10 of the present example was identical to example 1, except that gadolinium oxide $Gd_2O_3$ and lithium nitrate $LiNO_3$ were used in place of europium oxide $Eu_2O_3$ and potassium nitrite $KNO_2$ to fabricate the sensor electrode 3.

Sensing in Dry Atmosphere

FIG. 11 is a response curve representing the electromotive force of the nitrogen oxide sensor 10 induced by the NO gas contained in dry measurement samples. As shown in the figure, the electromotive force (output) of the nitrogen oxide sensor 10 in a dry atmosphere monotonically increased with a decrease in the NO gas concentration and monotonically decreased with an increase in the NO gas concentration. The response time was as short as about 10 minutes.

Referring to FIG. 12, the reactions in the nitrogen oxide sensor 10 are reversible, because the electromotive force assumed reproducible values both in cases where the NO gas concentration increased (white squares) and where it decreased (black circles) (good one-to-one correspondence observable between the electromotive forces and the logarithms of the NO gas concentrations).

Still referring to the figure, electromotive forces were plotted against NO gas concentrations for dry measurement sample, so as to determine the number of electrons transferred in the reaction, assigned n, in equation (7). Results showed n=2.77 for increasing NO gas concentrations and n=2.51 for decreasing NO gas concentrations. Both values differed by great amounts from the theoretical number of electrons transferred in the reaction calculated from equation (7) (n=1.00; see a slant line in the figure) by great amounts.

Example 4

Figure 13:
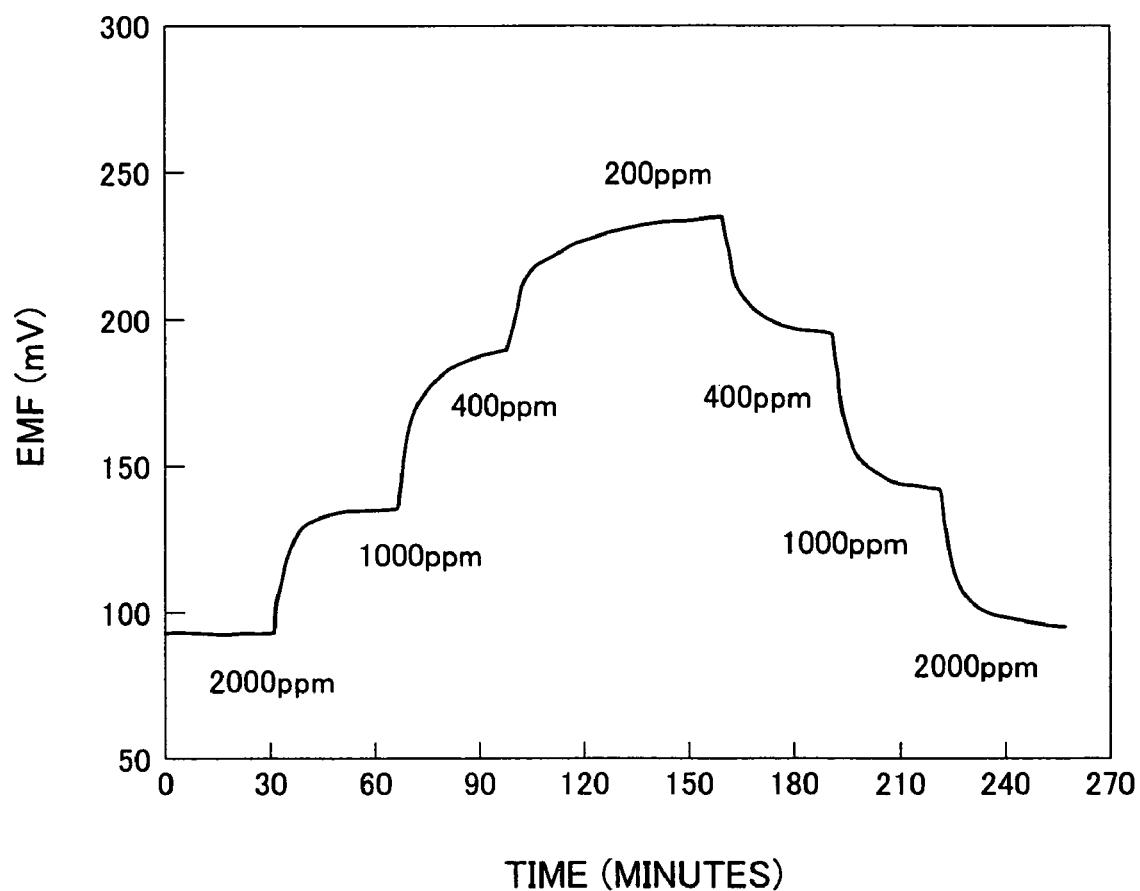
FIG. 13 is a graph of a response curve representing the electromotive force of an example 4-1 nitrogen oxide sensor induced by a NO gas contained in a dry measurement sample.
Figure 14:
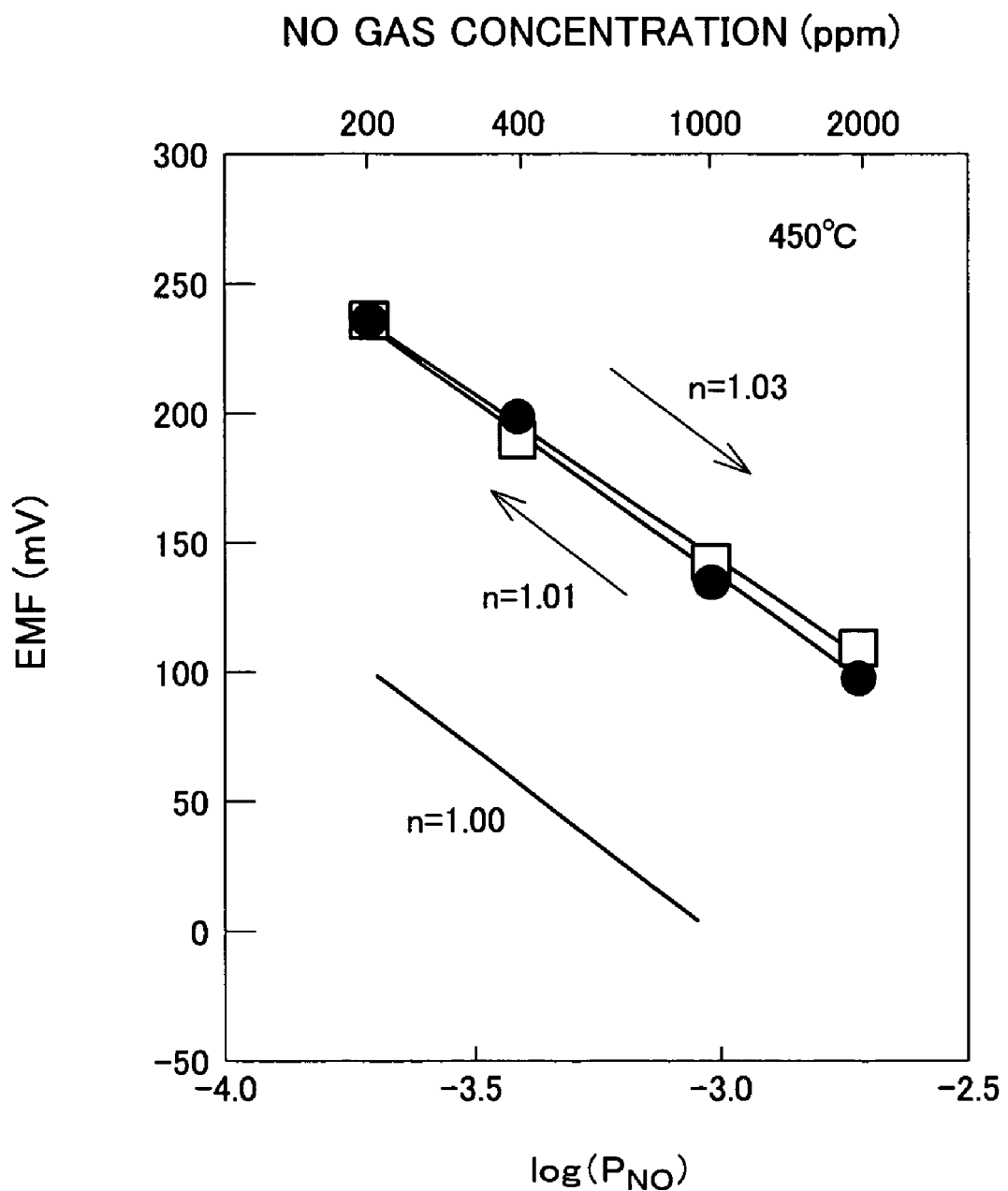
FIG. 14 is a graph showing the electromotive force of the example 4 nitrogen oxide sensor induced by a NO gas contained in a dry measurement sample as in FIG. 13, with the NO gas concentration being varied both in increasing/decreasing directions.

The following will describe a nitrogen oxide sensor which is another example of the present invention, as well as the solid electrolyte, the oxide ion conductor, and the sensor electrode, in reference to FIG. 1 and FIG. 13 to FIG. 14. Note that the present example, $0.35Gd_2O_3$-$0.3KNO_2$, which showed a maximum permittivity, was used as the sensor electrode; $(Al_{0.2}Zr_{0.8})_{20/19}Nb(PO_4)_3$ as the solid electrolyte (multivalent cation conductor) similarly to example 1; and $(ZrO_2)_{0.92}(Y_2O_3)_{0.08}$ as the oxide ion conductor. Note also that in the present example, a NO gas (example 4-1), a $NO_2$ gas (example 4-2), and a $NO/NO_2$ gas mixture (example 4-3) were used as the nitrogen oxide.

Example 4-1

Solid Electrolyte and Oxide Ion Conductor

The nitrogen oxide sensor of the present example is constructed as shown in the schematic of FIG. 1. The solid electrolyte 1 and the oxide ion conductor 2, which were components of the nitrogen oxide sensor 10 of the present example, were fabricated identically to example 1.

Sensor Electrode

The sensor electrode 3, which was a component of the nitrogen oxide sensor 10 of the present example, was fabricated identically to example 1, except that the europium oxide $Eu_2O_3$ in example 1 was replaced with gadolinium oxide $Gd_2O_3$.

Nitrogen Oxide Sensor

The nitrogen oxide sensor 10 of the present example, as mentioned earlier, was fabricated identically to example 1, except that gadolinium oxide $Gd_2O_3$ was used in place of europium oxide $Eu_2O_3$ in the fabrication of the sensor electrode 3.

Conditions in Nitrogen Oxide Measurement

Nitrogen oxide measurement was conducted identically to example 1.

Sensing Principles

As mentioned earlier, the nitrogen oxide sensor 10 of the present example was almost identical to example 1, except that gadolinium oxide $Gd_2O_3$ was used in place of europium oxide $Eu_2O_3$ to fabricate the sensor electrode 3.

Therefore, it would be safe to assume that almost the same reactions as in equations (1) to (7) discussed in example 1 took place except that $Eu_2O_3$ is replaced by $Gd_2O_3$ in equation (1).

Sensing in Dry Atmosphere

FIG. 13 is a response curve representing the electromotive force of the nitrogen oxide sensor 10 induced by the NO gas contained in dry measurement samples. As shown in the figure, the electromotive force (output) of the nitrogen oxide sensor 10 in a dry atmosphere monotonically decreased with an increase in the NO gas concentration and monotonically increased with a decrease in the NO gas concentration. The response time was as short as 7 minutes to 10 minutes.

Referring to FIG. 14, the reactions in the nitrogen oxide sensor 10 are reversible, because the electromotive force assumed reproducible values both in cases where the NO gas concentration increased (white squares) and where it decreased (black circles) (good one-to-one correspondence observable between the electromotive forces and the logarithms of the NO gas concentrations).

Still referring to the figure, electromotive forces were plotted against NO gas concentrations for dry samples, so as to determine the number of electrons transferred in the reaction, assigned n, in equation (7). Results showed n=1.03 for increasing NO gas concentrations and n=1.01 for decreasing NO gas concentrations. Both values well fit the theoretical number of electrons transferred in the reaction calculated from equation (7) (n=1.00; see a slant line in the figure).

Thus, the present example demonstrated that the NO gas concentration was accurately measured through the measurement of the sensor output.

Example 4-2

$NO_2$ Gas Measurement

Measurement was conducted on a $NO_2$ gas as the nitrogen oxide, similarly to the measurement on a NO gas in example 4-1.

Sensing in Dry Atmosphere

Figure 15:
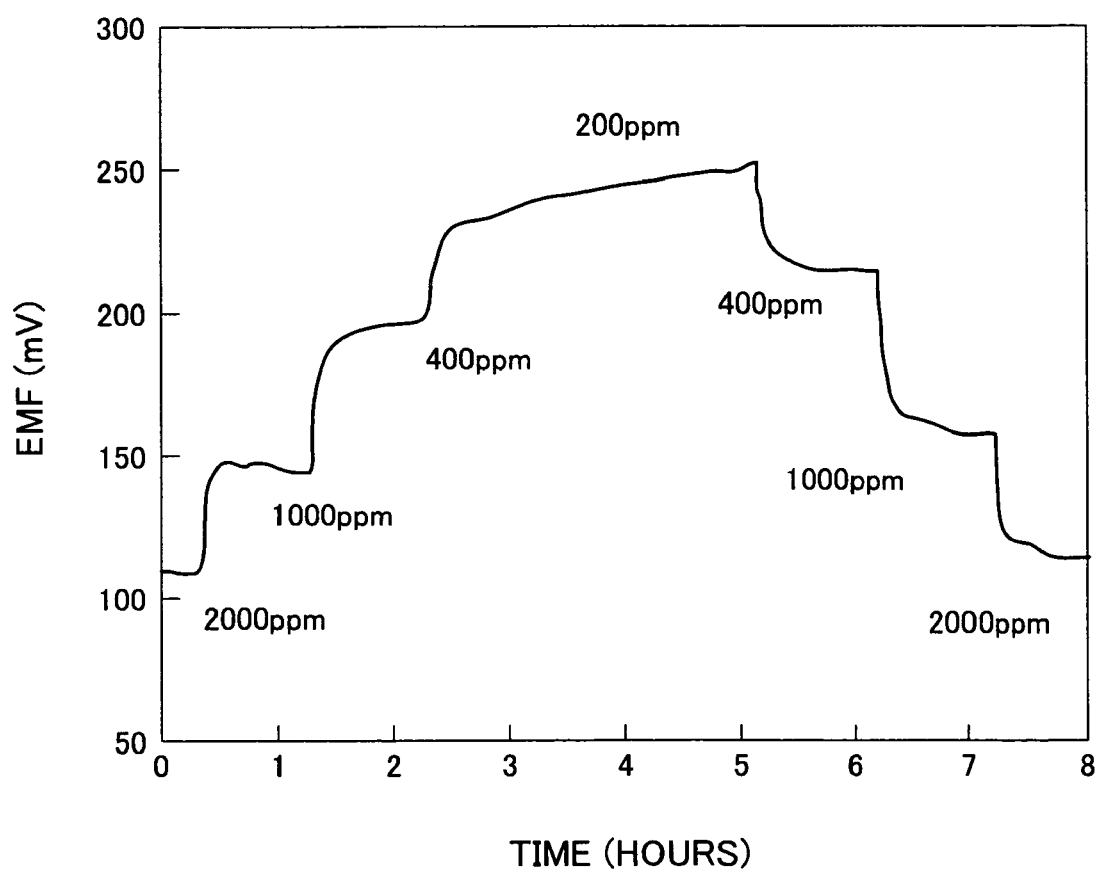
FIG. 15 is a graph of a response curve representing the electromotive force of an example 4 nitrogen oxide sensor induced by a $NO_2$ gas contained in a dry measurement sample.

FIG. 15 is a response curve representing the electromotive force of the nitrogen oxide sensor 10 induced by the $NO_2$ gas contained in dry measurement samples. As shown in the figure, the electromotive force (output) of the nitrogen oxide sensor 10 in a dry atmosphere monotonically increased with a decrease in the $NO_2$ gas concentration and monotonically decreased with an increase in the NO gas concentration. The response time was from 10 minutes to 30 minutes. The electromotive force decreased with an increase in the concentration. Conversely, when the concentration was changed back to its original value, the sensor output returned practically to its original value. This confirms that the $NO_2$ gas concentration can be measured reversibly, similarly to the case of a NO gas concentration.

Figure 16:
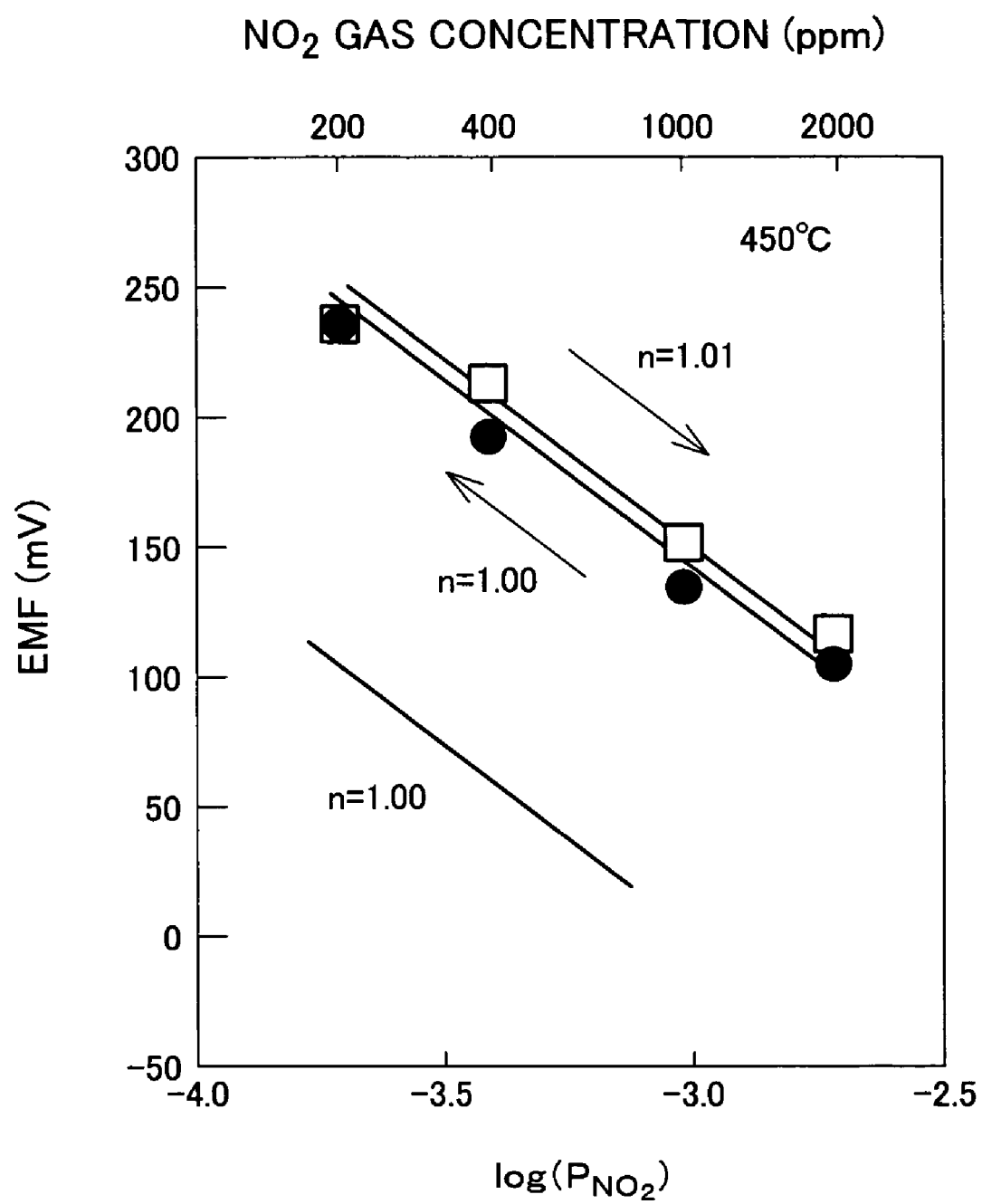
FIG. 16 is a graph showing the electromotive force of the example 4 nitrogen oxide sensor induced by a $NO_2$ gas contained in a dry measurement sample as in FIG. 15, with the $NO_2$ gas concentration being varied both in increasing/decreasing directions.

Referring to FIG. 16, the reactions in the nitrogen oxide sensor 10 are reversible, because the electromotive force assumed reproducible values both in cases where the $NO_2$ gas concentration increased (white squares) and where it decreased (black circles) (good one-to-one correspondence observable between the electromotive forces and the logarithms of the $NO_2$ gas concentrations).

Still referring to the figure, electromotive forces were plotted against NO gas concentrations for dry samples, so as to determine the number of electrons transferred in the reaction, assigned n, in equation (7). Results showed n=1.01 for increasing $NO_2$ gas concentrations and n=1.00 for decreasing $NO_2$ gas concentrations. Both values well fit the theoretical number of electrons transferred in the reaction calculated from equation (7) (n=1.00, see a slant line in the figure).

Thus, the present example demonstrated that the $NO_2$ gas concentration was accurately measured through the measurement of the sensor output.

Example 4-3

$NO/NO_2$ Gas Mixture Measurement

Figure 17:
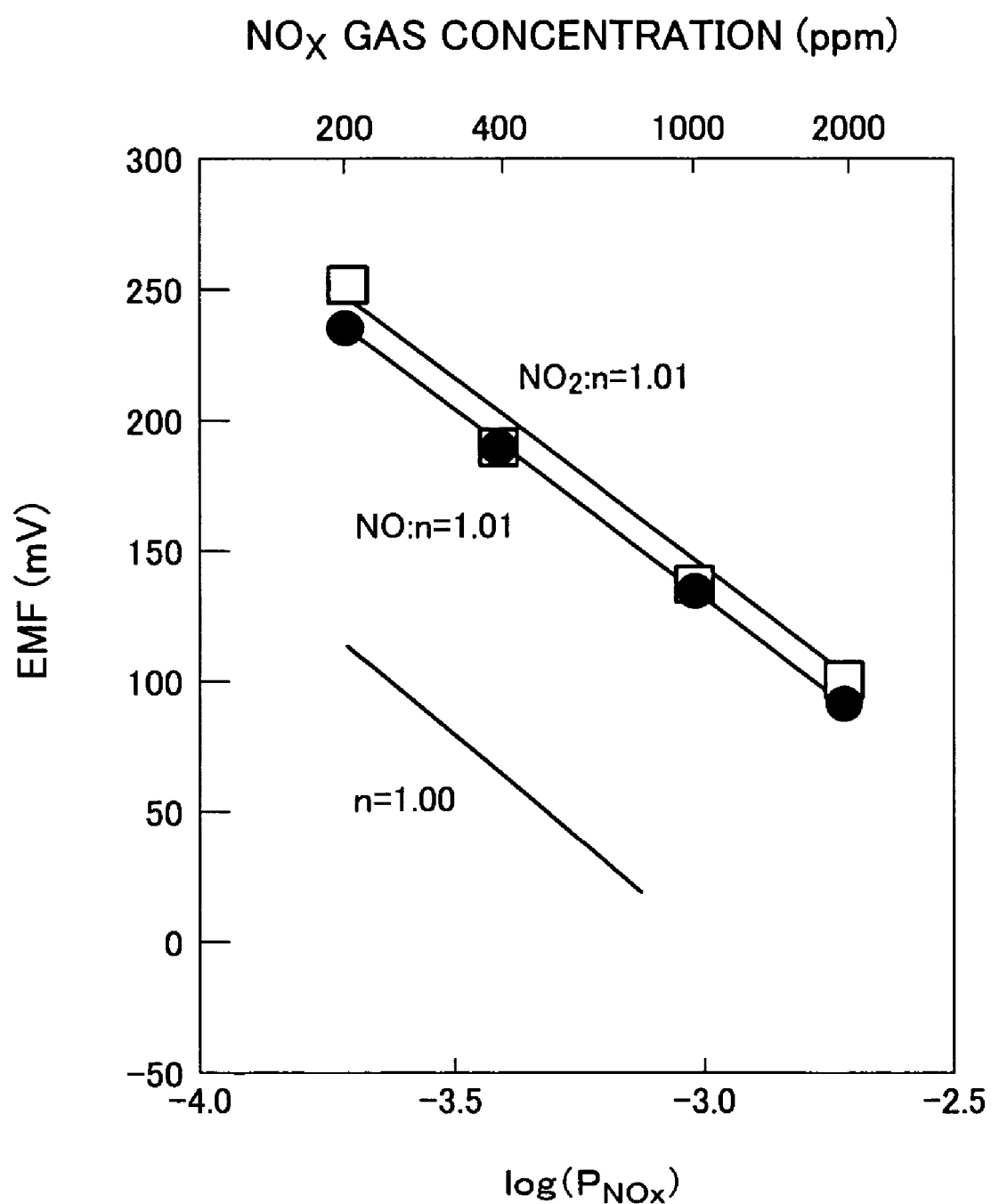
FIG. 17 is a graph showing the electromotive force of the example 4 nitrogen oxide sensor induced by a $NO/NO_2$ gas mixture contained in a dry measurement sample, with the $NO/NO_2$ gas concentration being varied both in increasing/decreasing directions.

FIG. 17 is a graph showing the NOx gas concentration dependence of the electromotive force of the example 4 nitrogen oxide sensor. As shown in the figure, the electromotive force for the NO gas (black circles) and the electromotive force for the $NO_2$ gas (white squares) assumed almost equal values at the same concentration. This demonstrates that the nitrogen oxide sensor 10 of the present example can measure the NOx concentration of a $NO/NO_2$ mixed gas system.

Sensing in Dry Atmosphere

Figure 18:
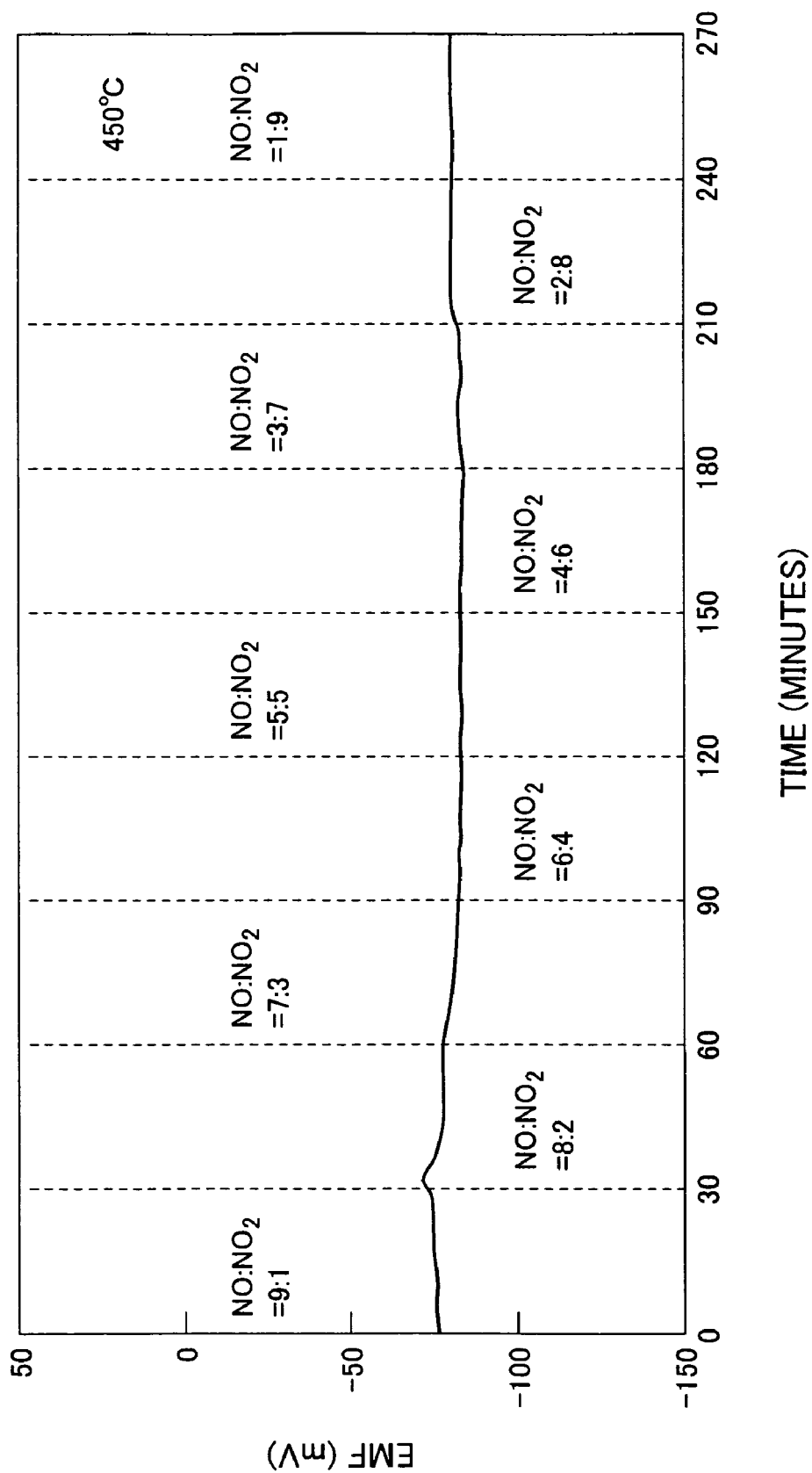
FIG. 18 is a graph of a response curve representing the electromotive force of the example 4 nitrogen oxide sensor where the $NO/NO_2$ gas mix ratio in the dry measurement sample is varied.

FIG. 18 is a response curve representing the electromotive force of the nitrogen oxide sensor 10 for the NO gas in dry measurement samples. The NOx concentration was fixed at 2000 ppm, while the $NO/NO_2$ mix ratio was varied to take many different values. The electromotive force value differed from values indicated in FIGS. 13 and 15 for the 2000 ppm gas flow, because different batches were used from examples 4-1 and 4-2. However, the electromotive force does not vary with a change in the $NO/NO_2$ mix ratio. This confirms that the nitrogen oxide sensor 10 can measure the NOx concentration of a $NO/NO_2$ mixed gas system.

The foregoing description has clearly shown that the nitrogen oxide sensor, including $0.35Gd_2O_3$-$0.3KNO_2$ as the sensor electrode, $(Al_{0.2}Zr_{0.8})_{20/19}Nb(PO_4)_3$ as the solid electrolyte, and $(ZrO_2)_{0.92}(Y_2O_3)_{0.08}$ as the oxide ion conductor, has sufficiently sensor capability for NOx gas leaking into the atmosphere in industrial facilities, for example. In addition, with a nitrite as the sensor electrode, the sensor exhibits electromotive force dependence of its NOx gas concentration which matches well with theoretical values, which demonstrates that the nitrogen oxide concentration can be accurately measured through the sensor's electromotive force. Further, with the nitrite sensor electrode, the sensor's electromotive force takes practically equal values at equal gas concentrations regardless of whether the nitrogen oxide concentration is being varied in increasing or decreasing direction. Thus, the NOx concentration can measured quickly and in a reversible manner.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

As detailed in the foregoing, the nitrogen oxide sensor in accordance with the present invention electrode contains a solid solution of a nitrate or nitrite of an alkali metal and an oxide of a rare-earth element.

Therefore, the sensor electrode is highly water-insoluble and suitable to nitrogen oxide sensing, especially, in a humid atmosphere containing water vapor. When the sensor electrode is incorporated, for example, in a nitrogen oxide sensor based on a solid electrolyte, the nitrogen oxide sensor comes to exhibit highly practical features, especially nitrogen oxide sensing capability with good responsiveness in a humid atmosphere containing water vapor.

The nitrogen oxide sensor in accordance with the present invention contains the sensor electrode, the solid electrolyte, and the oxide ion conductor. The sensor electrode and the oxide ion conductor are provided in contact with a surface of the solid electrolyte. The solid electrolyte conducts magnesium ions, aluminum ions, rare earth ions, zirconium ions, or hafnium ions.

Therefore, the nitrogen oxide sensor exhibits highly practical features, especially high water-insolubility and suitability to the measurement of nitrogen oxides in a humid atmosphere containing water vapor.

The invention claimed is:

1. A nitrogen oxide sensor electrode, comprising: a solid solution of a nitrate or nitrite of an alkali metal; and an oxide of a rare-earth element.

2. The nitrogen oxide sensor electrode as set forth in claim 1, wherein said oxide is $Eu_2O_3$, $Y_2O_3$, or $Gd_2O_3$.

3. The nitrogen oxide sensor electrode as set forth in claim 1, wherein said nitrate or nitrite is a nitrite of an alkali metal.

4. The nitrogen oxide sensor electrode as set forth in claim 3, wherein said nitrite is $KNO_2$.

5. A nitrogen oxide sensor, comprising: the nitrogen oxide sensor electrode as set forth in claim 1; a solid electrolyte; and an oxide ion conductor, wherein:

the nitrogen oxide sensor electrode and the oxide ion conductor are provided in contact with a surface of the solid electrolyte; and the solid electrolyte conducts magnesium ions, aluminum ions, rare earth ions, zirconium ions, or hafnium ions.

6. The nitrogen oxide sensor as set forth in claim 5, wherein the solid electrolyte is sandwiched between the nitrogen oxide sensor electrode and the oxide ion conductor.

7. The nitrogen oxide sensor as set forth in claim 5, wherein the solid electrolyte has a Nasicon or β-iron sulfate crystal structure.

8. The nitrogen oxide sensor as set forth in claim 7, wherein the solid electrolyte is a complex of $Mg_{1+X}Zr_4P_6O_{24+X}$ ($0<X\leq0.4$) and $Zr_2O(PO_4)_2$ or a solid solution, $Mg_{1-2Y}(Zr_{1-Y}Nb_Y)_4P_6O_{24}$ ($0\leq Y<\frac{1}{2}$), conducting magnesium ions.

9. The nitrogen oxide sensor as set forth in claim 7, wherein the solid electrolyte has a composition, $(Al_{0.2}Zr_{0.8})_{20/19}Nb(PO_4)_3$, conducting aluminum ions.

10. The nitrogen oxide sensor as set forth in claim 7, wherein the solid electrolyte has a composition, $R_{1/3}Zr_2(PO_4)_3$, conducting rare earth ions, where R is a rare earth atom.

11. The nitrogen oxide sensor as set forth in claim 7, wherein the solid electrolyte has a composition, $ZrNb(PO_4)_3$, conducting zirconium ions.

12. The nitrogen oxide sensor as set forth in claim 7, wherein the solid electrolyte has a composition, $HfNb(PO_4)_3$, conducting hafnium ions.

13. The nitrogen oxide sensor as set forth in claim 5, wherein the oxide ion conductor is made of at least one of the group consisting of fully stabilized zirconia, cerium oxide, bismuth oxide, hafnium oxide, thorium oxide, and lanthanum gallate.

14. The nitrogen oxide sensor as set forth in claim 5, wherein the solid electrolyte is 0.1 mm to 1.5 mm thick.

15. The nitrogen oxide sensor as set forth in claim 5, wherein the oxide ion conductor is 0.1 mm to 1.5 mm thick.

16. The nitrogen oxide sensor electrode as set forth in claim 2, wherein said nitrate or nitrite is a nitrite of an alkali metal.

17. A nitrogen oxide sensor, comprising: the nitrogen oxide sensor electrode as set forth in claim 2; a solid electrolyte; and an oxide ion conductor, wherein:
the nitrogen oxide sensor electrode and the oxide ion conductor are provided in contact with a surface of the solid electrolyte; and
the solid electrolyte conducts magnesium ions, aluminum ions, rare earth ions, zirconium ions, or hafnium ions.

18. A nitrogen oxide sensor, comprising: the nitrogen oxide sensor electrode as set forth in claim 3; a solid electrolyte; and an oxide ion conductor, wherein:
the nitrogen oxide sensor electrode and the oxide ion conductor are provided in contact with a surface of the solid electrolyte; and
the solid electrolyte conducts magnesium ions, aluminum ions, rare earth ions, zirconium ions, or hafnium ions.

19. A nitrogen oxide sensor, comprising: the nitrogen oxide sensor electrode as set forth in claim 4; a solid electrolyte; and an oxide ion conductor, wherein:
the nitrogen oxide sensor electrode and the oxide ion conductor are provided in contact with a surface of the solid electrolyte; and
the solid electrolyte conducts magnesium ions, aluminum ions, rare earth ions, zirconium ions, or hafnium ions.

20. The nitrogen oxide sensor as set forth in claim 6, wherein the solid electrolyte has a Nasicon or β-iron sulfate crystal structure.

21. The nitrogen oxide sensor as set forth in claim 5, wherein the nitrogen oxide sensor electrode is of a board shape and 0.1 mm to 1.5 mm thick.

* * * * *

UNITED STATES PATENT AND TRADEMARK OFFICE
CERTIFICATE OF CORRECTION

PATENT NO. : 7,537,678 B2  
APPLICATION NO. : 10/512307  
DATED : May 26, 2009  
INVENTOR(S) : Nobuhito Imanaka Page 1 of 1

It is certified that error appears in the above-identified patent and that said Letters Patent is hereby corrected as shown below:

Title Page, Item (54) should read:
(54)    NITROGEN OXIDE SENSOR ELECTRODE AND NITROGEN OXIDE SENSOR INCORPORATING THE SAME Signed and Sealed this Eleventh Day of August, 2009

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,537,678 B2 | Page 1 of 1 |
| APPLICATION NO. | : 10/512307 | |
| DATED | : May 26, 2009 | |
| INVENTOR(S) | : Nobuhito Imanaka | |

It is certified that error appears in the above-identified patent and that said Letters Patent is hereby corrected as shown below:

Title Page, Item (54) and Column 1, lines 1 and 2, should read:
    NITROGEN OXIDE SENSOR ELECTRODE AND NITROGEN OXIDE
    SENSOR INCORPORATING THE SAME This certificate supersedes the Certificate of Correction issued August 11, 2009.

Signed and Sealed this

First Day of September, 2009

David J. Kappos
*Director of the United States Patent and Trademark Office*